United States Patent
Kim et al.

(10) Patent No.: US 7,455,917 B2
(45) Date of Patent: Nov. 25, 2008

(54) ORGANIC COMPOUND AND ORGANIC LIGHT EMITTING DEVICE USING THE SAME

(75) Inventors: Kong Kyeom Kim, Daejeon (KR); Min Jeong Lee, Seoul (KR); Yeon Hwan Kim, Goyang-si (KR); Jun Gi Jang, Daejeon (KR)

(73) Assignee: LG Chem, Ltd. (KR)

( * ) Notice: Subject to any disclaimer, the term of this patent is extended or adjusted under 35 U.S.C. 154(b) by 278 days.

(21) Appl. No.: 10/967,620

(22) Filed: Oct. 18, 2004

(65) Prior Publication Data

US 2005/0123800 A1      Jun. 9, 2005

(30) Foreign Application Priority Data

Oct. 17, 2003   (KR)   ................. 10-2003-0072680

(51) Int. Cl.
*H01L 51/54* (2006.01)
*H05B 33/14* (2006.01)
*C09K 11/06* (2006.01)
*C07F 5/02* (2006.01)

(52) U.S. Cl. ............... 428/690; 428/917; 313/504; 313/506; 257/40; 257/E51.05; 544/180; 544/198; 544/212; 564/8; 568/3

(58) Field of Classification Search ........... 544/198; 568/3
See application file for complete search history.

(56) References Cited

U.S. PATENT DOCUMENTS

| | | | | |
|---|---|---|---|---|
| 3,663,209 | A * | 5/1972 | Sato et al. | .............. 430/523 |
| 4,865,762 | A | 9/1989 | Kreuder et al. | ......... 252/299.01 |
| 6,150,042 | A | 11/2000 | Tamano et al. | ............. 428/690 |
| 2003/0180575 | A1* | 9/2003 | Ise | ........................ 428/690 |

FOREIGN PATENT DOCUMENTS

JP   2-279788   11/1990

(Continued)

OTHER PUBLICATIONS

Coad et al., Journal of Organic Chemistry, (1996), vol. 61, pp. 6666-6672.*

(Continued)

*Primary Examiner*—Dawn L. Garrett
*Assistant Examiner*—Brett A Crouse
(74) *Attorney, Agent, or Firm*—Cantor Colburn LLP

(57) ABSTRACT

Disclosed is a compound represented by formula 1:
[formula 1]

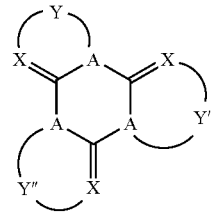

[formula 1]

wherein each of A, X, Y, Y' and Y" has the same meaning as described herein. When used in an organic light emitting device, the compound represented by formula 1 has at least one function selected from the group consisting of hole injection, hole transport, light emitting, electron transport, electron injection, etc., depending on the type of each unit forming the trimer or substituents in each unit. An organic light emitting device is also disclosed. The organic light emitting device includes a first electrode, an organic film having one or more layers and a second electrode, laminated successively, wherein at least one layer of the organic film includes at least one compound represented by formula 1.

5 Claims, 3 Drawing Sheets

FOREIGN PATENT DOCUMENTS

JP          10-502065          2/1998

OTHER PUBLICATIONS

Lavagnino et al., Journal of Heterocyclic Chemistry, (1972), vol. 9, No. 1, pp. 149-150.*
Ishida et al., Bulletin of the Chemical Society of Japan, (1975), vol. 48, No. 3, pp. 956-959.*
Coad et al., Journal of the American Chemical Society, (1994), vol. 116, pp. 391-392.*
Apen et al., Chemistry of Materials, (1994), vol. 6, pp. 831-835.*
Takeuchi et al., Journal of Organic Chemistry, (1979), vol. 44, No. 24, pp. 4243-4246.*
PCT International Search Report; PCT/KR2004/002661; Date: Feb. 7, 2006.
"Charge Recombination Electroluminescence in Organic Thin-Gilm Devices Without Charge Injection From External Electrodes"; Authors: Tetsuo Tsutsu, Sang-Bond Lee, and Katsuhiko Fujita; Applied Physics Letters, vol. 85, No. 12; Sep. 20, 2004.
"Electroluminesence of Doped Organic Thin Films"; Authors: C.W. Tang, S.A. VanSlyke, C.H. Chen; J. Appl. Phys. 85 (9), May 1, 1989; pp. 3610-3616.
"1,2,4-Triazole Derivative as an Electron Transport Layer in Organic Electroluminescent Devices"; Authors: Juji Kido, Chikau Ohtaki, Kenichi Hongawa, Katsuro Okuyama and Katsutoshi Nagai; Jpn. J. Appl. Phys. vol. 32 (1993) pp. L917-L920; Part 2, No. 7A, Jul. 1, 1993.

* cited by examiner

ORGANIC COMPOUND AND ORGANIC LIGHT EMITTING DEVICE USING THE SAME

TECHNICAL FIELD

The present invention relates to a new organic compound and an organic light emitting device using the same.

BACKGROUND ART

In general, the so-called "organic light emitting" phenomenon (organic electroluminescence) refers to a phenomenon in which electric energy is transformed into light energy by means of an organic substance. Particularly, when an organic film is disposed between an anode and a cathode and then electric potential is applied between both electrodes, holes and electrons are injected into the organic film from the anode and the cathode, respectively. When the holes and electrons injected as described above are recombined, excitons are formed. Further, when the exitons drop to a ground state, lights are emitted.

In addition to the above-described organic light emitting mechanism in which light emission is made by recombining of charges injected from both electrodes, there is another mechanism in which holes and electrons are not injected from external electrodes but are generated by an amphoteric charge-generating layer under the application of alternating current voltage, as in the case of a conventional inorganic thin film light emitting device, and the holes and electrons move to an organic thin film layer, resulting in light emission (*Appl. Phys. Lett.*, 85(12), 2382-2384).

Since POPE, KALLMAN, et al. found electro-luminescence in anthracene single crystal in 1963, active research and development into OLEDs (Organic Light Emitting Devices) have been made up to now. Recently, organic light emitting devices have been used in flat panel display devices, lighting devices, etc. Such organic light emitting devices have been developed so rapidly that performance as display devices is remarkably improved and various applied products are developed.

In order to manufacture more efficient organic light emitting devices, many attempts have been made to manufacture an organic film in the device in the form of a multilayer structure instead of a monolayer structure. Most of currently used organic light emitting devices have a structure in which an organic film and electrodes are deposited. The organic film generally has a multilayer structure including a hole injection layer, hole transport layer, light emitting layer, electron transport layer and an electron injection layer.

It is known that OLEDs are characterized by high brightness, high efficiency, low drive voltage, color changeability, low cost, etc. However, in order to have such characteristics, each layer forming an organic film in a device (for example, a hole injection layer, hole transport layer, light emitting layer, electron transport layer and electron injection layer) must be formed of more stable and efficient materials.

A method of doping a light emitting host with a fluorescent compound so as to increase the light emitting efficiency of a multilayer-structured OLED was disclosed. Particularly, according to Tang, et al. (*J. Appl. Phys.* Vol. 65 (1989), p. 3610), light emitting efficiency can be improved by mixing a fluorescent compound having a high quantum efficiency (for example, coumarin pigments or pyran derivatives) in a small amount with a light emitting host. In this case, light having a desired wavelength can be obtained depending on the type of the fluorescent compound. However, when Alq3 is used as electron transport material and drive voltage is increased to obtain high brightness, green light emission based on Alq3 may be observed in addition to light emission based on the doped fluorescent compound. This is problematic in terms of color purity, particularly when the color of light to be emitted is blue. It is known that such a problem results from a narrow band gap between the HOMO (highest occupied molecular orbital) and the LUMO (lowest unoccupied molecular orbital) of Alq3. Such a narrow band gap results in exciton diffusion from a light emitting layer to Alq3, thereby causing light emission based on Alq3.

The use of hole block material has been reported as another method for increasing light emitting efficiency of OLEDs, wherein the hole block material includes 3-(4-biphenylyl)-4-phenyl-5-(4-tert-butylphenyl)-1,2,4-triazole (TAZ), bathocuproine (BCP), etc. (*Jpn. J. App. Phys.* Part 2, 1993, 32, L917). However, the above-mentioned materials show poor durability and have a serious problem of deterioration of a device, particularly when the device is subjected to continuous light emission while being stored at high temperature. Moreover, there are additional problems in that the above-mentioned materials should be provided as a layer separated from a light emitting layer, and that drive voltage increases due to a large band gap between the HOMO and the LUMO when the materials are used.

Therefore, in order to overcome the problems occurring in the prior art and to further improve characteristics of OLEDs, it is necessary to develop more stable and efficient materials that may be used in OLEDs.

DISCLOSURE OF THE INVENTION

Figure 1:
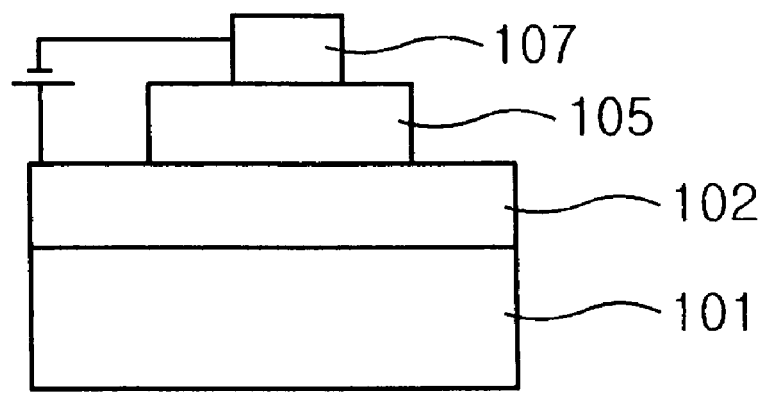
FIGS. 1 to 5 are schematic views each illustrating the structure of an organic light emitting device (OLED) that may be applied to the present invention, wherein reference numeral 101 is a substrate, 102 is an anode, 103 is a hole injection layer, 104 is a hole transport layer, 105 is a light emitting layer, 108 is a hole block layer, 106 is an electron transport layer and 107 is a cathode 107.

It is an object of the present invention to improve durability and/or efficiency of an organic light emitting device by an organic substance capable of carrying out at least one function selected from the group consisting of hole injection, hole transport, hole block, light emitting, electron transport, electron injection, and buffering between an anode and a hole injection layer, wherein the organic substance is designed by using a cyclic trimer core structure represented by the following formula 1.

According to an aspect of the present invention, there is provided a compound represented by formula 1:

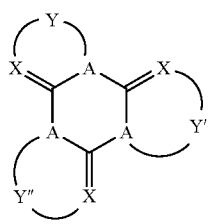

[formula 1]

wherein

A is B or N;

X is N or $CR_0$, wherein $R_0$ is selected from the group consisting of a hydrogen atom (H), halogen atom, nitrile group (CN), nitro group ($NO_2$), formyl group, acetyl group, benzoyl group, amide group, styryl group, acetylene group, quinoline group, quinazoline group, phenanthroline group, cuproine group, anthraquinone group, benzoquinone group, quinone group, acridine group, substituted or non-substituted alkyl group, substituted or non-substituted aryl group, substituted or non-substituted aralkyl group, substituted or non-substituted arylamine group, substituted or non-substituted alkylamine group, substituted or non-substituted aralkylamine group, and substituted or non-substituted heterocyclic group; and each of Y, Y' and Y" represents a substituted or non-substituted aromatic heterocycle that includes a 5-membered aromatic heterocycle containing A and X as ring members or a 6-membered aromatic heterocycle containing A and X as ring members, wherein Y, Y' and Y" are identical or different.

The number of substituents present in Y, Y' and Y" is at least one and the substituents are identical or different, each substituent being selected from the group consisting of a halogen atom, nitrile group (CN), nitro group ($NO_2$), formyl group, acetyl group, benzoyl group, amide group, styryl group, acetyelene group, quinoline group, quinazoline group, phenanthroline group, cuproine group, anthraquinone group, benzoquinone group, quinone group, acridine group, substituted or non-substituted alkyl group, substituted or non-substituted aryl group, substituted or non-substituted aralkyl group, substituted or non-substituted arylamine group, substituted or non-substituted alkylamine group, substituted or non-substituted aralkylamine group, and substituted or non-substituted heterocyclic group, wherein in some cases two substituents adjacent to each other may form a fused ring together.

According to another aspect of the present invention, there is provided an organic light emitting device including a first electrode, an organic film having one or more layers and a second electrode, laminated successively, wherein at least one layer of the organic film includes at least one compound represented by formula 1.

Hereinafter, the present invention will be explained in detail.

The present invention provides a compound represented by formula 1.

The compound represented by formula 1 is an organic substance including a cyclic trimer core structure. The compound is capable of carrying out at least one function selected from the group consisting of hole injection, hole transport, hole block, light emitting, electron transport, electron injection, and buffering between an anode and a hole injection layer, depending on the type of each unit forming the trimer or substituents in each unit. Particularly, the function of buffering between an anode and a hole injection layer is required when interfacial contact between them is poor, or when direct hole injection into a hole injection layer is not made properly. Many compounds are known to carry out at least one function selected from the group consisting of hole injection, hole transport, hole block, light emitting, electron transport, electron injection, and buffering between an anode and a hole injection layer. Most of them generally include a substituted or non-substituted aromatic or heteroaromatic group.

Meanwhile, all kinds of compounds capable of carrying out at least one function selected from the group consisting of hole injection, hole transport, hole block, light emitting, electron transport, electron injection, and buffering between an anode and a hole injection layer can be prepared by varying the type of each trimer-forming unit or substituents present in each unit from the organic substance represented by the above formula 1 including a cyclic trimer core structure. Heretofore, it has not been known that all kinds of compounds capable of carrying out at least one function needed for a desired organic light emitting device can be prepared by varying the type of each unit or substituents from one basic structure.

Organic substances that function as hole injection materials are compounds facilitating hole injection from an anode. Preferably, such compounds have ionization potential suitable for hole injection from an anode, high interfacial adhesion to an anode, non-absorbability in the visible light range, etc. Particular examples of units or substituents capable of performing a function of a hole injection include organic substances of metal porphyrin, oligothiophen, arylamine series, organic substances of hexanitrile hexaazatriphenylene, quinacridone series, organic substances of perylene series, conductive polymers based on anthraquinone, polyaniline, and polythiophene or polymers such as dopants, but are not limited thereto.

Organic substances that function as hole transport materials preferably have high hole mobility and high LUMO energy level for electron blocking. Particular examples of units or substituents capable of performing a function of a hole transport may include organic substances of arylamine series, conductive polymers and block copolymers having both conjugated portions and non-conjugated portions, but are not limited thereto. Particular examples thereof include triarylamine derivatives, amines having a bulky aromatic group, starburst aromatic amines, spirofluorene-containing amines, crosslinked amines and anthracene-based compounds.

Organic substances that function as electron transport materials are those having an electron withdrawing group. Units or substituents capable of performing a function of an electron transport may include compounds containing a functional group capable of withdrawing electrons by resonance (for example cyano, oxadiazole or triazole group). Particular exmples thereof include 8-hydroxyquinolone-Al complex; complexes including Alq3; organic radical compounds; and hydroxy- flavone-metal complexes, but are not limited thereto.

Organic substances that function as light emitting materials are those having moieties capable of emitting light by accepting and recombining holes and electrons and may include fluorescent materials and phosphorescent materials. Particular examples of units or substituents capable of performing a function of a light emitting include 8-hydroxyquinoline aluminum complex (Alq3); compounds of carbazole series; dimerized styryl compounds; BAlq3; 10-hydroxybenzoquinoline-metal compounds; compounds of benzoxazole, benzthiazole and benzimidazole series; polymers based on poly(p-phenylenevinylene) series; polymers based on poly-phenylenevinylene (PPV); spiro compounds; and compounds of polyfluorene, rubrene and anthracene series, but are not limited thereto.

Meanwhile, an organic substance designed by using the cyclic trimer core structure represented by formula 1 has a molecular weight higher than that of each monomer forming the trimer. Accordingly, it has high thermal stability, thereby improving durability of an OLED including an organic film formed by using the same. Additionally, when a monomeric organic substance used in a light emitting layer is trimerized, the resultant molecular weight increases accordingly, and thus it is possible to obtain an organic substance having a long wavelength shifted from a short wavelength (for example, from blue to red). Further, the compound represented by formula 1 having a trimerized structure provides a suitable band gap between the HOMO and the LUMO and energy value compared to each monomer forming the trimer, thereby reducing drive voltage.

Additionally, in the cyclic trimer core structure represented by formula 1, the saturated 6-membered ring having three heteroatoms (A) forms a non-planar (for example, chair-like) structure like the structure of cyclohexane, contrary to a flat aromatic ring. Therefore, three units, i.e.,

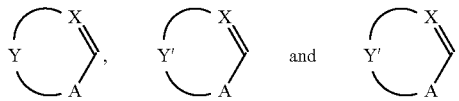

that are bonded symmetrically to the 6-membered ring form a non-planar propeller-like structure in which they are distorted symmetrically to one another, so that steric hindrance among the three units can be reduced. Further, if each of the units (generally, substituted or non-substituted aromatic compounds) forming the trimer is present as a monomer, the aromatic compounds are laminated together in the form of a flat plane and thus permit intermolecular interaction. However, if monomers are trimerized into the core structure represented by formula 1, their amorphous characteristics can be exerted more. Therefore, it is possible to prevent the breakdown of a device caused by crystallization resulting from the Joule heat generated during the operation of an OLED. Further, the cyclic trimer core structure represented by formula 1 has three units bonded symmetrically to the non-planar 6-membered ring and thus it is possible to design organic substances having structures that are not excessively planar but ordered. The above-described characteristics are useful for an organic substance used in a hole transport layer or electron transport layer.

The cyclic trimer represented by formula 1 does not permit extension of conjugation among units because of the saturated 6-membered ring, and thus each unit can function independently from each other. Therefore, it is possible to contemplate each unit individually and to facilitate molecular designs. For example, each unit can be derived from a monomer having a function different from each other. Additionally, when a monomeric organic substance used in a light emitting layer is trimerized into a cyclic form at meta-positions as depicted in formula 1, its molecular weight increases followed by a wavelength shift to a long wavelength. In this case, the saturated 6-membered ring prevents further extension of conjugation, and thus can reduce a shift range compared to a linear polymer obtained from the monomer.

In formula 1, A is preferably a nitrogen atom (N).

In formula 1, X is preferably a nitrogen atom (N).

In formula 1, when substituents attached to Y, Y' and Y'' include an alkyl group, the length of the alkyl group does not significantly affect the compound of formula 1 in carrying out at least one function selected from the group consisting of hole injection, hole transport, hole block, light emitting, electron transport, electron injection, and buffering between an anode and a hole injection layer. Light absorption or emission in an electronic device can be affected by the conjugation length of a functional compound. Because the length of an alkyl group included in the compound does not affect the conjugation length of the compound, it has no direct effect on the wavelength of the compound or on characteristics of a device. However, the length of an alkyl group may affect the selection of a method of applying the compound to an OLED (for example, a vacuum deposition method or a solution coating method). Therefore, there is no particular limitation in length of alkyl groups that may be included in the structure represented by formula 1.

One example of the compound represented by formula 1 is a compound represented by the following formula 2:

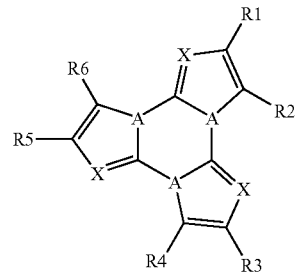

[Formula 2]

wherein

A and X are the same as defined above with regard to formula 1; and

R1 to R6 are identical or different and each is selected from the group consisting of a hydrogen atom (H), halogen atom, nitrile group (CN), nitro group ($NO_2$), formyl group, acetyl group, benzoyl group, amide group, styryl group, acetylene group, quinoline group, quinazoline group, phenanthroline group, cuproine group, anthraquinone group, benzoquinone group, quinone group, acridine group, substituted or non-substituted alkyl group, substituted or non-substituted aryl group, substituted or non-substituted aralkyl group, substituted or non-substituted arylamine group, substituted or non-substituted alkylamine group, substituted or non-substituted aralkylamine group, and substituted or non-substituted heterocyclic group, wherein in some cases R1 and R2, R3 and R4, and R5 and R6 may form a fused ring with each other.

Another example of the compound represented by formula 1 is a compound represented by the following formula 3:

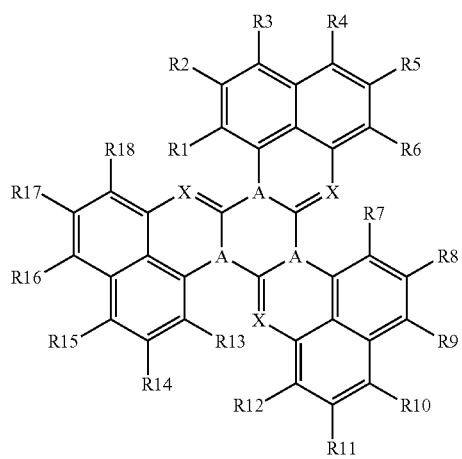

[Formula 3]

wherein

A and X are the same as defined above with regard to formula 1; and

R1 to R18 are identical or different and have the same meanings as R1 to R6 in the above formula 2, wherein in some cases each of R1 to R18 may form a fused ring together with a substituent adjacent thereto.

Non-limitative examples of the substituents in formulae 1-3 (for example $R_0$ to R18) will be described hereinafter.

Halogen atoms include a fluorine (F), chlorine (Cl), bromine (Br) and iodine (I) atoms.

Alkyl groups preferably have 1 to 20 of carbon atoms (C1-C20) and include linear alkyl groups such as methyl, ethyl, propyl, hexyl, etc., and branched alkyl groups such as isopropyl, tert-butyl, etc.

Aryl groups include monocyclic aromatic cycles such as phenyl, etc., and multicyclic aromatic cycles such as naphthyl, anthryl, pyrene, perylene, etc.

Aralkyl groups include C1-C20 alkyl groups substituted with aromatic hydrocarbons such as phenyl, biphenyl, naphthyl, terphenyl, anthryl, pyrene, perylene, etc.

Arylamine groups include amine groups substituted with aromatic hydrocarbons such as phenyl, biphenyl, naphthyl, terphenyl, anthryl, pyrene, perylene, etc.

Alkylamine groups include amine groups substituted with C1-C20 aliphatic hydrocarbons.

Aralkylamine groups include amine groups substituted with aromatic hydrocarbons such as phenyl, biphenyl, naphthyl, terphenyl, anthryl, pyrene, perylene, etc., and C1-C20 aliphatic hydrocarbons.

Heterocyclic groups include pyrrolyl, thienyl, indole, oxazole, imidazole, thiazole, pyridyl, pyrimidine, piperazine, thiophene, furan, pyridazinyl, etc.

In formulae 2 and 3, fused rings formed by each of R1 to R18 with a substituent adjacent thereto include pyrrole, furan, thiophene, indole, oxazole, imidazole, thiazole, pyridine, pyrizine, benzene, naphthalene, pyrazine, quinoline, quinazoline, phenanthroline, cuproine, anthraquinone, benzoquinone, quinone, acridine, etc.

Further, each of substituted alkyl, aryl, aralkyl, arylamine, alkylamine, aralkylamine and heterocyclic groups in $R_0$ to R18 may have one or more substituents selected from the group consisting of a halogen atom including fluorine, chlorine, bromine and iodine, nitrile, nitro, formyl, acetyl, arylamine, alkylamine, aralkylamine, benzoyl, amide, styryl, acetylene, phenyl, naphathyl, anthryl, pyrene, perylene, pyridyl, pyridazyl, pyrrolyl, imidazolyl, quinolyl, anthrone, acridone, acridine, etc.

Particular examples of the compound represented by formula 1 include the compounds represented by formulae 1-1 to 1-46, but are not limited thereto:

[Formula 1-1]

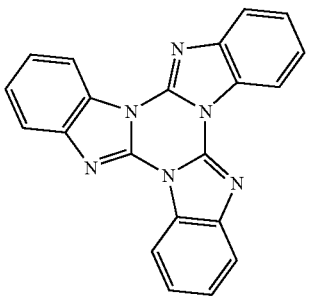

[Formula 1-2]

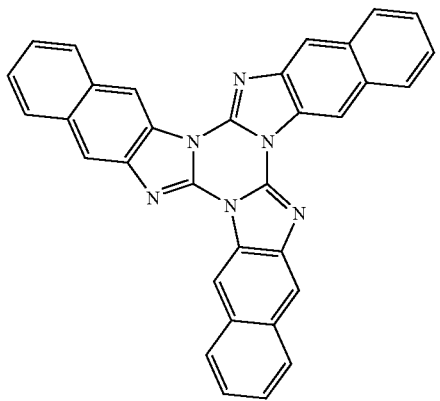

[Formula 1-3]

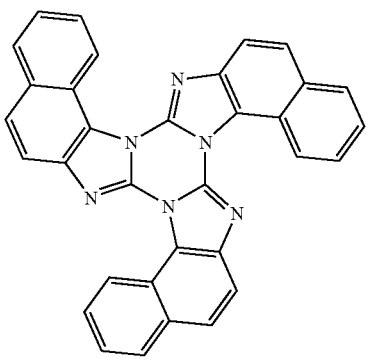

[Formula 1-4]

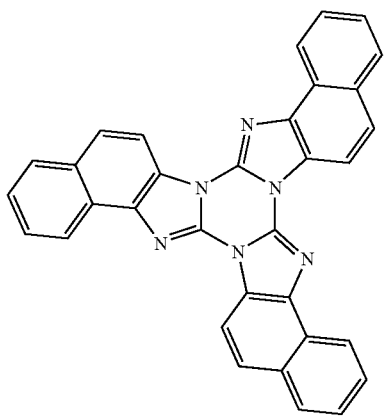

-continued
[Formula 1-5]
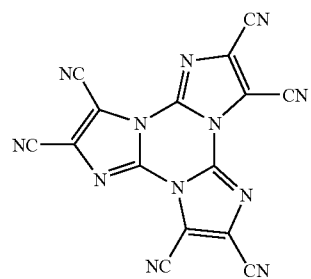
[Formula 1-6]
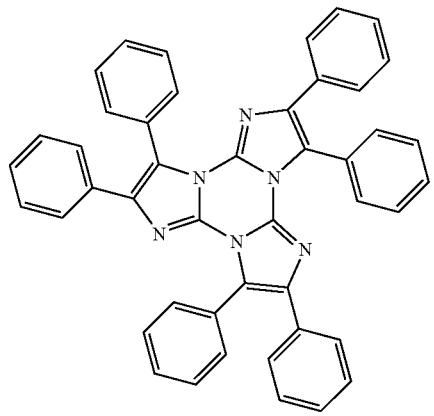
[Formula 1-7]
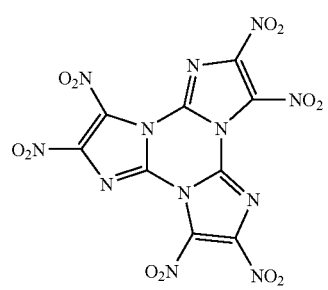
[Formula 1-8]
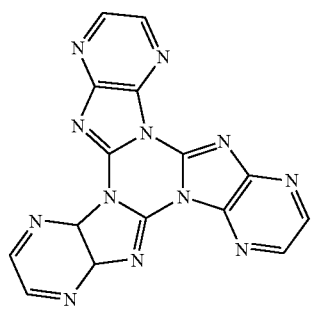
[Formula 1-9]
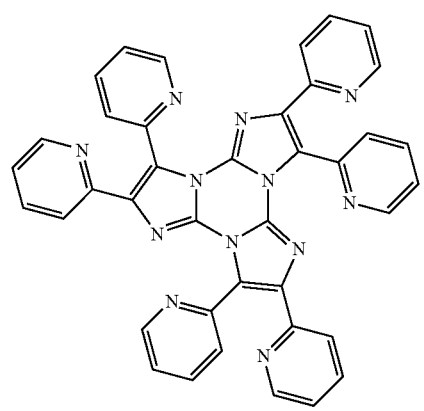
[Formula 1-10]
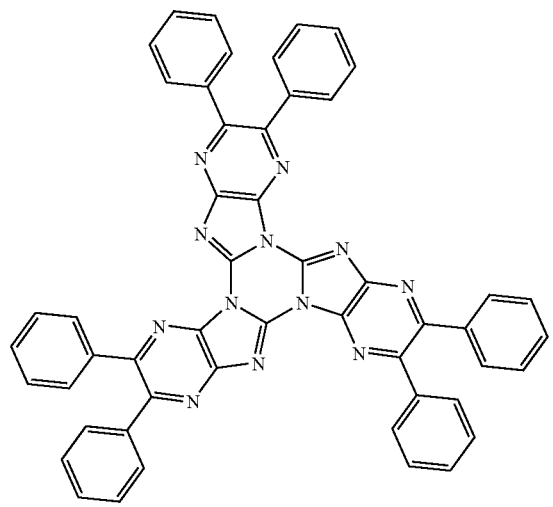

-continued
[Formula 1-11]
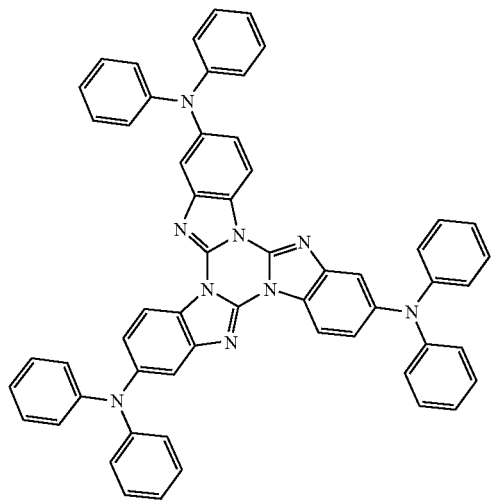
[Formula 1-12]
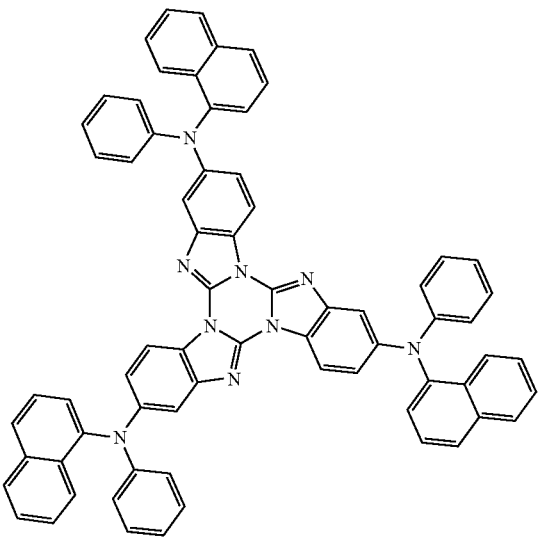
[Formula 1-13]
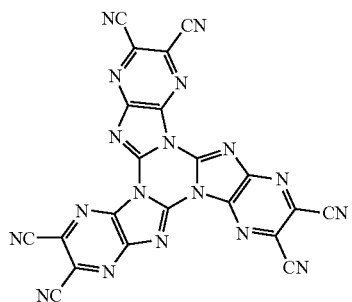
[Formula 1-14]
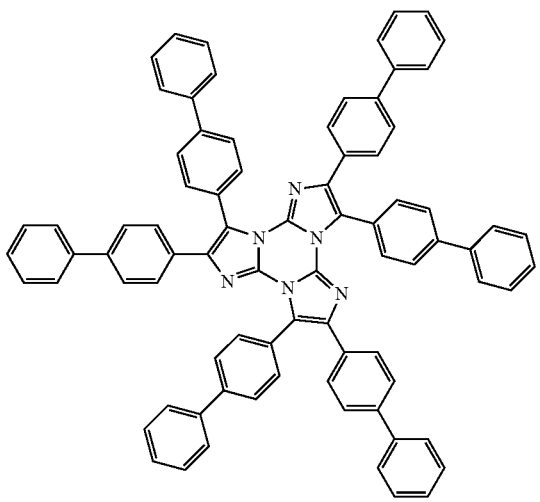
[Formula 1-15]
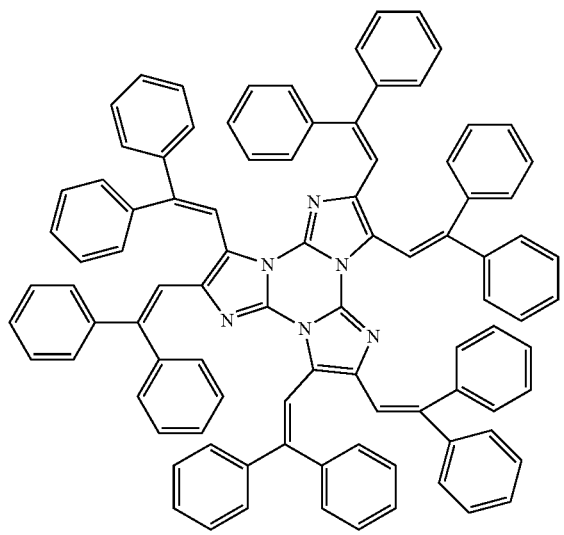
[Formula 1-16]
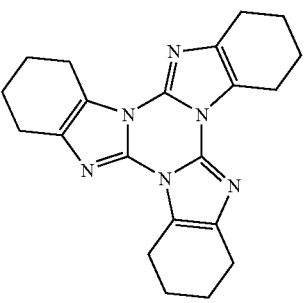

-continued
[Formula 1-17]
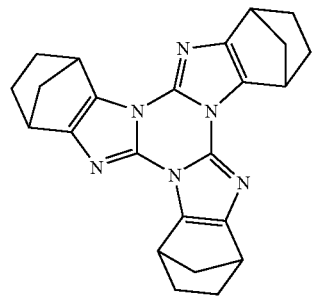
[Formula 1-18]
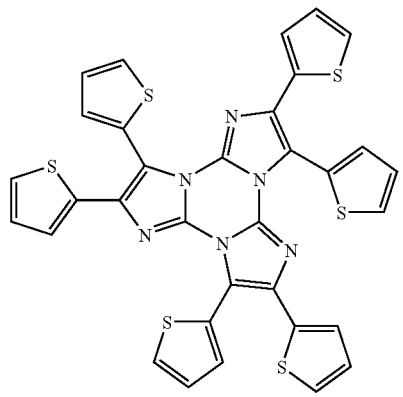
[Formula 1-19]
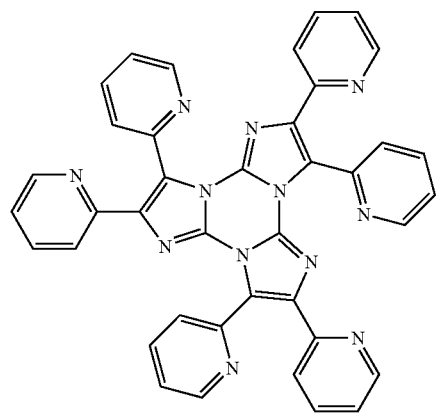
[Formula 1-20]
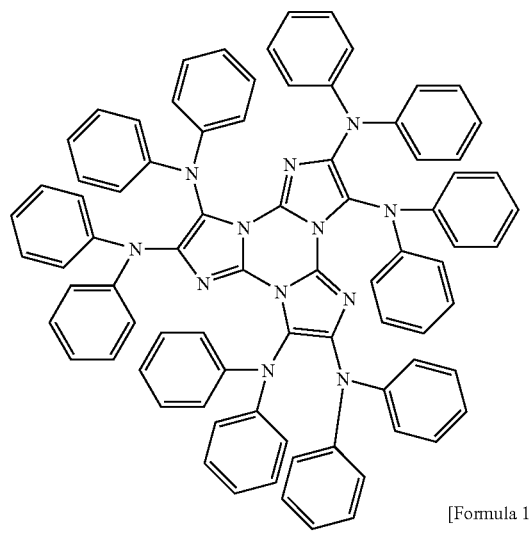
[Formula 1-21]
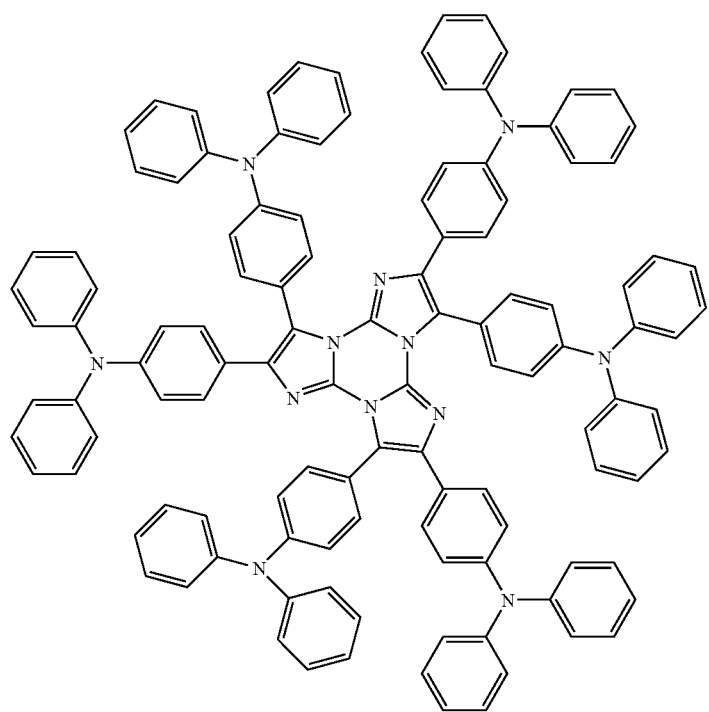

[Formula 1-22]
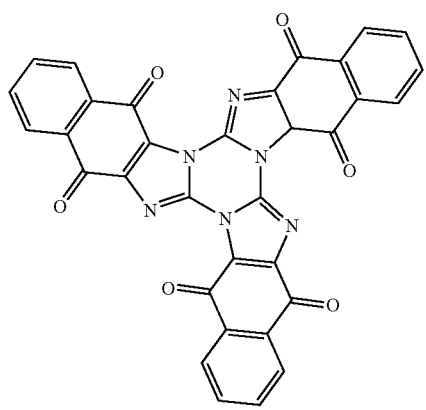
[Formula 1-23]
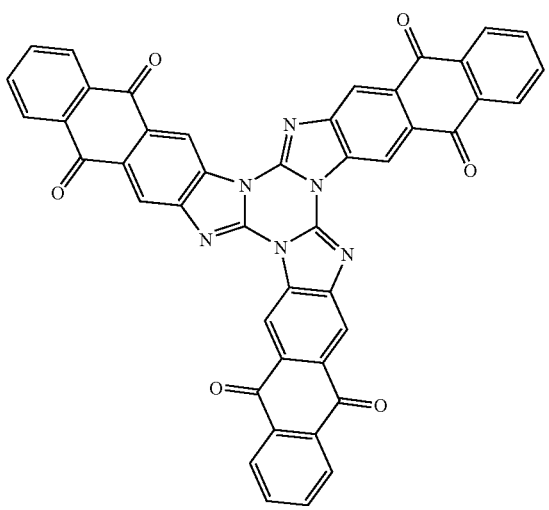
[Formula 1-24]
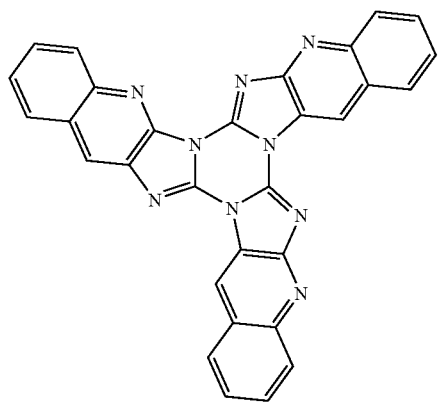
[Formula 1-25]
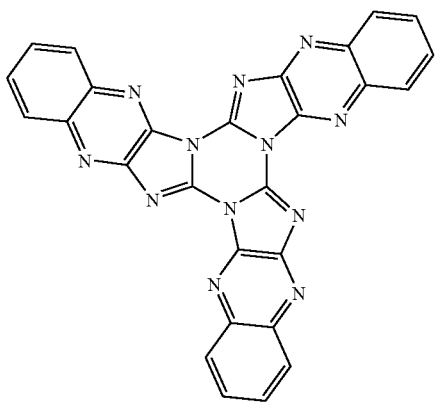
[Formula 1-26]
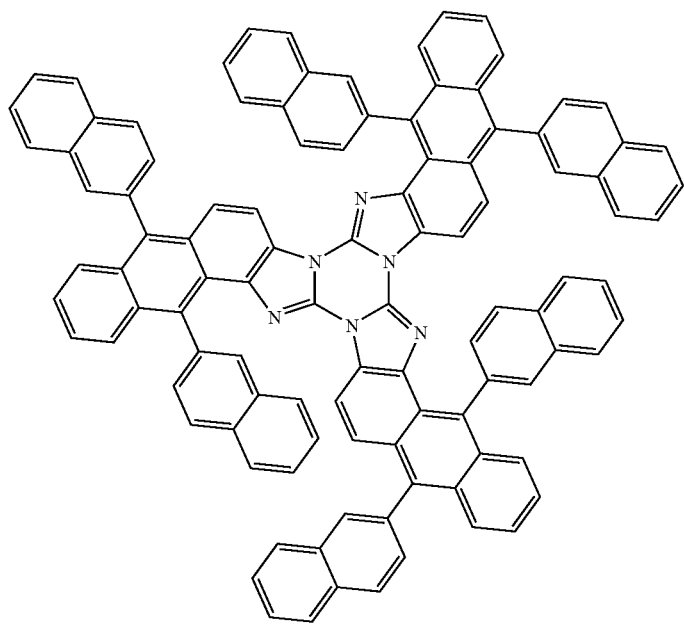

-continued
[Formula 1-27]
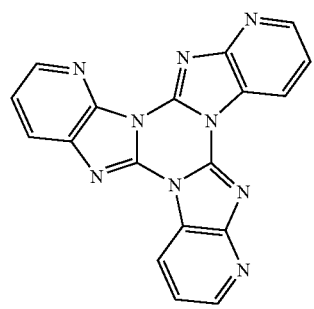
[Formula 1-28]
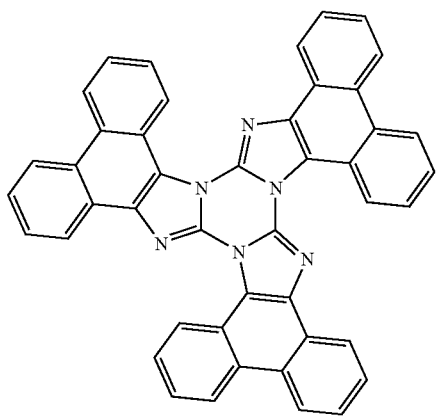
[Formula 1-29]
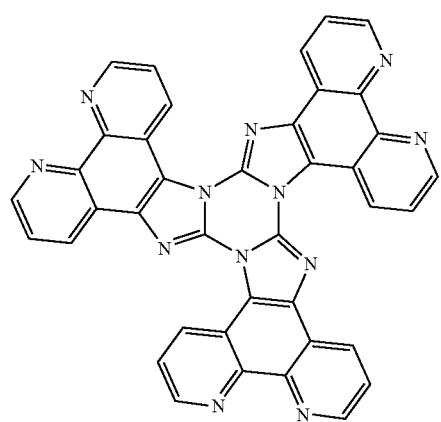
[Formula 1-30]
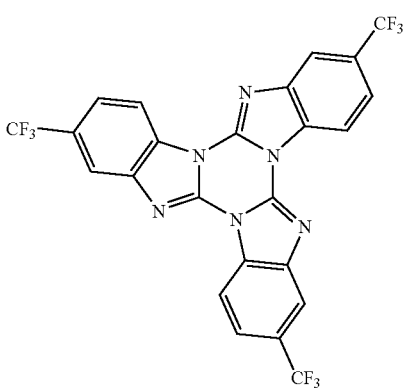
[Formula 1-31]
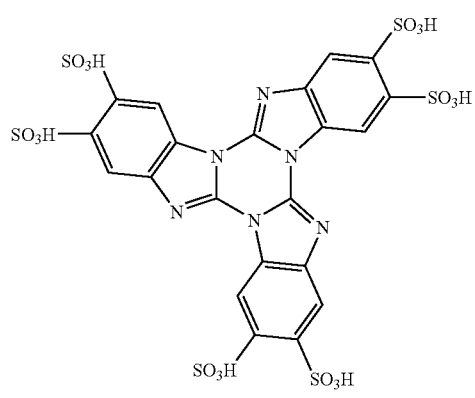
[Formula 1-32]
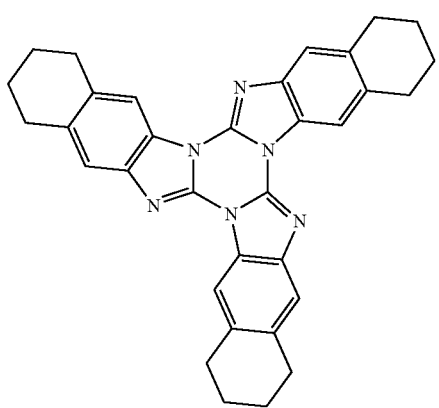

-continued
[Formula 1-33]
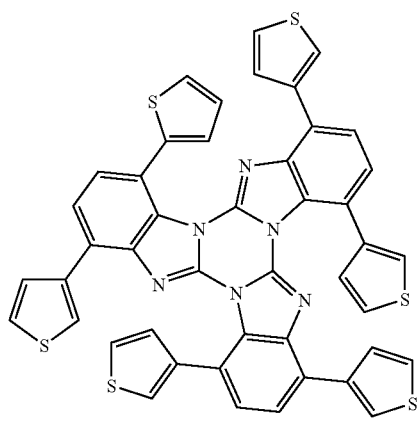
[Formula 1-34]
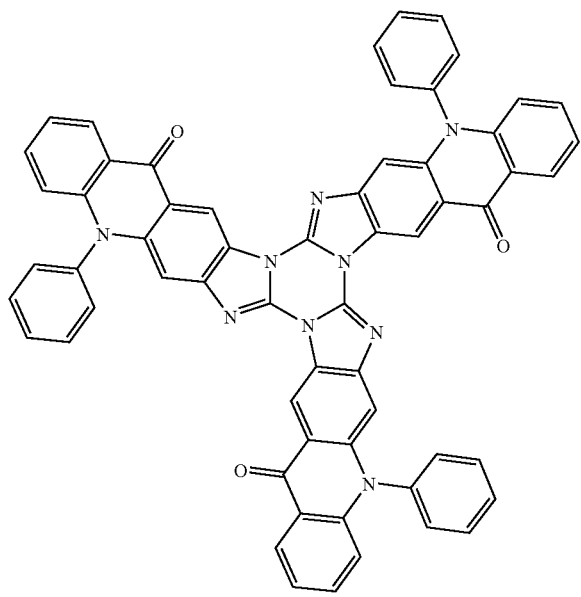
[Formula 1-35]
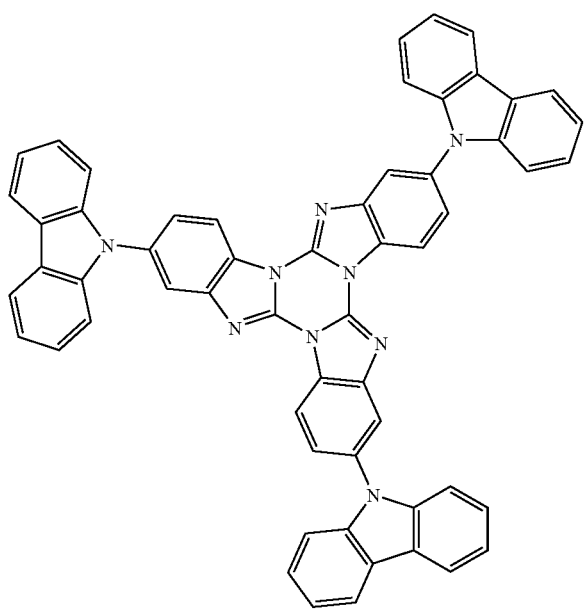

-continued
[Formula 1-36]
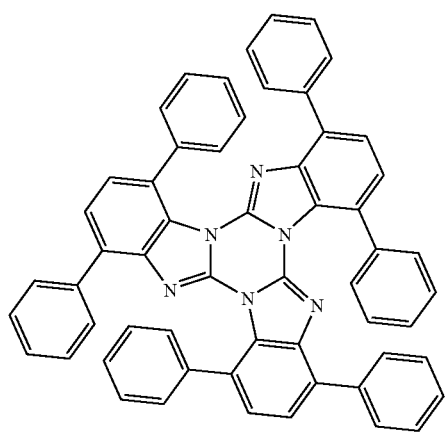
[Formula 1-37]
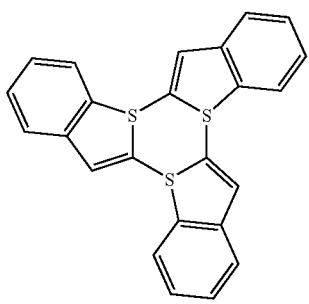
[Formula 1-38]
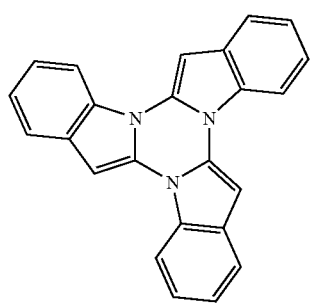
[Formula 1-39]
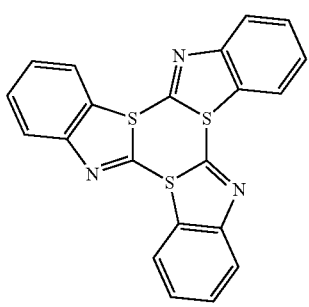
[Formula 1-40]
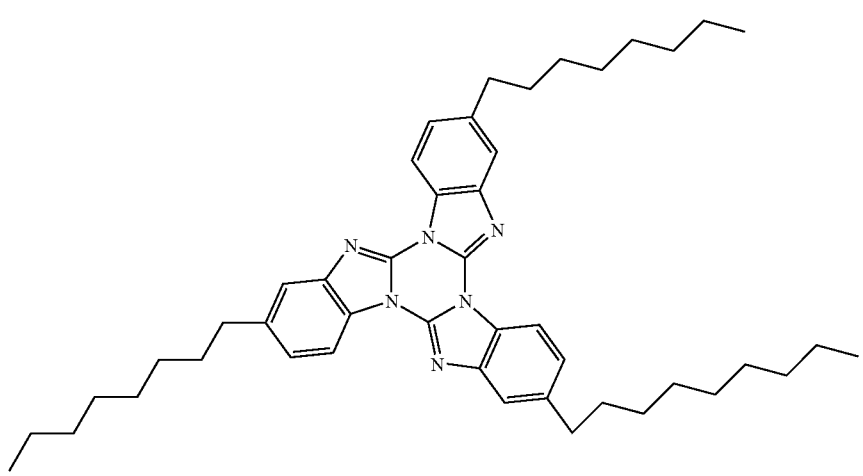

-continued
[Formula 1-41]
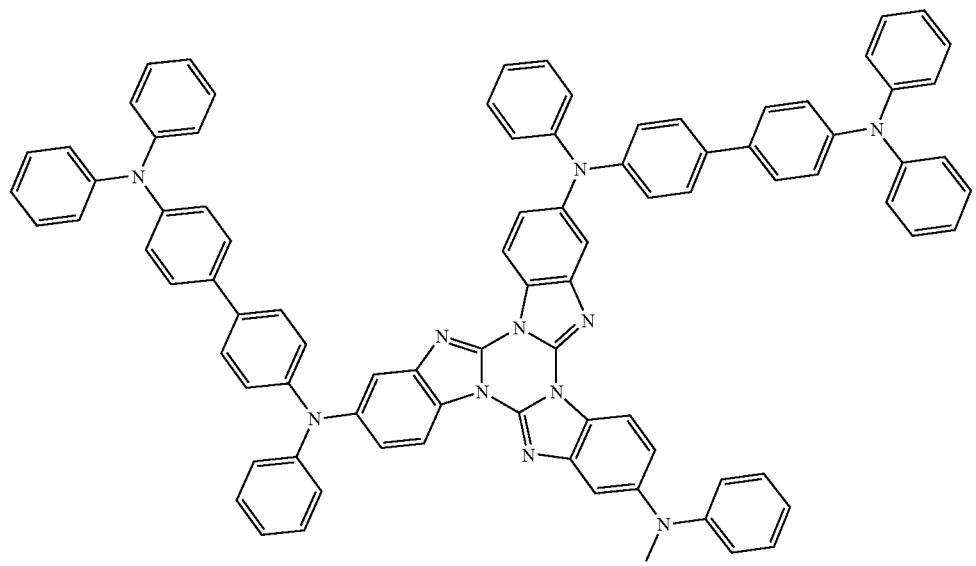
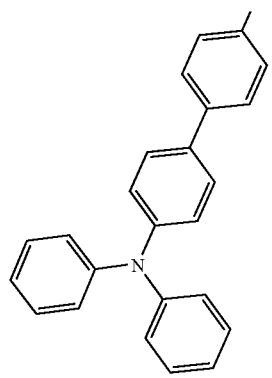
[Formula 1-42]
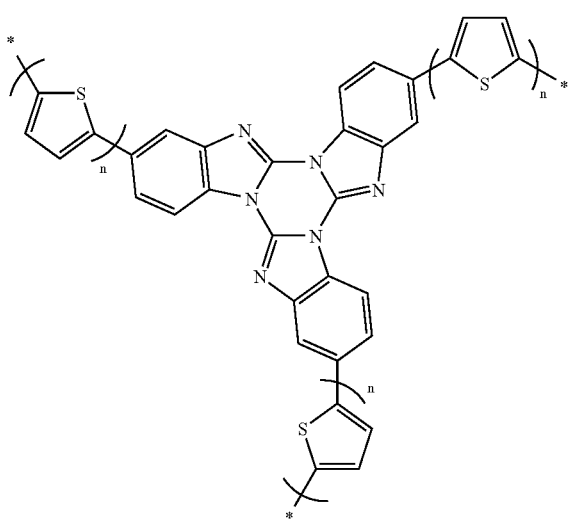

[Formula 1-43]

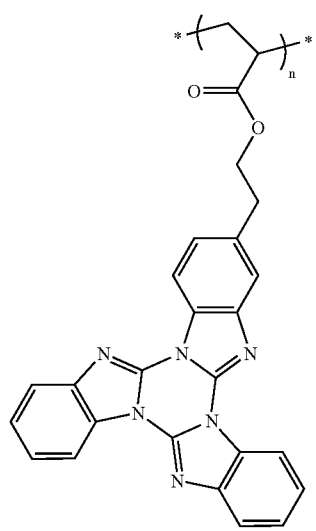

wherein n is an integer of at least 1.

[Formula 1-44]

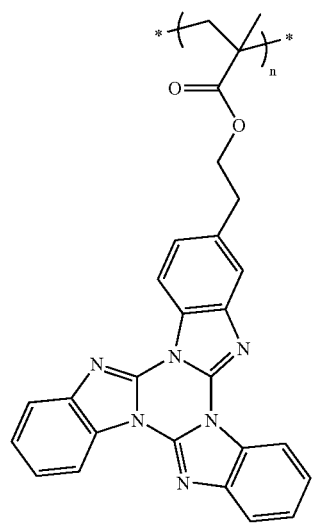

wherein n is an integer of at least 1.

[Formula 1-45]

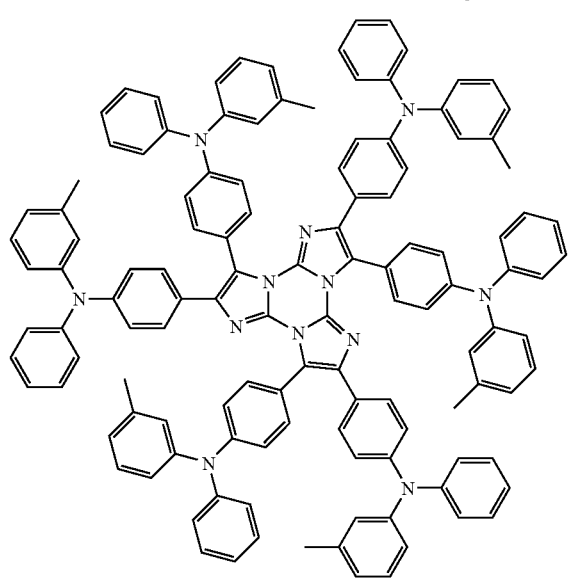

[Formula 1-46]

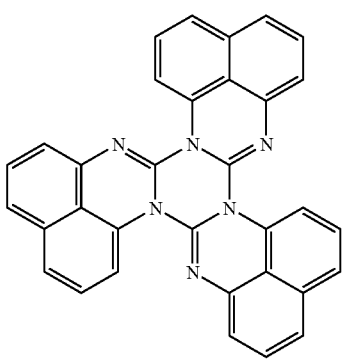

Additionally, the compound represented by formula 1 (for example, compound represented by formulae 1-1 or 1-35) can be used as a phosphorescence host, which may be used together with a phosphorescence dopant, in an organic phosphorescence light emitting device.

Meanwhile, as can be seen from the following Example 1, the compound represented by formula 1-1 is a substance that functions as an electron injection/transport material. Further, it can be seen indirectly that the compound represented by formula 1-1 is an n-type substance. Therefore, it can be seen that compounds having the compound represented by formula 1-1 as a core also function as electron injection/transport materials. Each monomer (benzimidazole) forming the trimeric compound represented by formula 1-1 cannot be applied to an organic film in an OLED by itself, because the band gap between the HOMO and the LUMO is large, it has no electron mobility and it has such a small molecular weight as to be sublimated easily. However, when a cyclic trimer represented by formula 1 is formed from such a monomer, it is possible to increase the molecular weight, to reduce the band gap between the HOMO and the LUMO and to impart electron mobility. Accordingly, even if a compound cannot function as a material for hole injection, hole transport, hole block, light emitting, electron transport, electron injection, and buffering between an anode and a hole injection layer, or the like, it is possible to cause the compound to have the above-described functions by forming a cyclic trimer represented by formula 1 from the compound as a monomer.

Meanwhile, the organic substance represented by formula 1-12 has a core represented by formula 1-1 having n-type characteristics and arylamine substituents imparting p-type characteristics, and thus can function as a hole transport material, as can be seen from the following Example 2. Therefore, compounds having a core represented by formula 1 can provide materials having p-type characteristics, n-type characteristics or amphoteric characteristics depending on the characteristics of substituents. Further, such characteristics depending on substituents determine an organic layer in an OLED that a compound represented by formula 1 can be used.

The compound represented by formula 1 can be prepared by using the following starting materials:

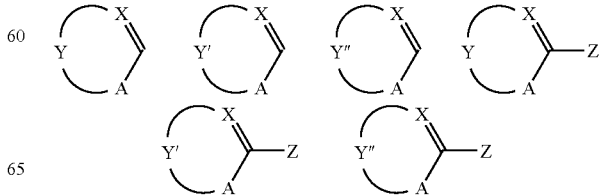

Particularly, non-limitative examples of the starting materials include the following compounds:

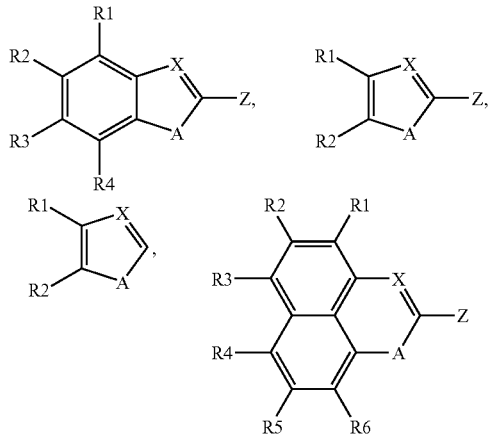

wherein A, X and R1 to R6 as substituents for Y, Y' and Y" are the same as defined above with regard to formula 1, 2 or 3; and Z is a halogen atom. Particularly, Z may be selected from the group consisting of F, Cl, Br and I.

According to the present invention, compounds represented by formula 1 may be prepared by trimerizing the starting materials and optionally introducing substituents to the resultant trimeric compounds if necessary. Trimerization or substituent introduction may be performed by using any conventional methods known to one skilled in the art. Further, solvents may be used in synthetic routes, if desired. For example, a desired trimer compound can be prepared by heating at least one compound selected from the above starting materials to 200-300° C. Preparation of trimer compounds will be explained in detail through the following Preparation Examples. However, it is to be understood that methods described in the following Preparation Examples can be modified by one skilled in the art in order to prepare compounds according to the present invention.

The present invention also provides an organic light emitting device (OLED) including a first electrode, an organic film having one or more layers and a second electrode, laminated successively, wherein at least one layer of the organic film contains at least one compound represented by formula 1.

In the OLED according to the present invention, the organic film containing the compound represented by formula 1 may be formed by using a vacuum deposition method or a solution coating method. Particular examples of the solution coating method include spin coating, dip coating, doctor blade coating, ink-jet printing or heat transfer method, but are not limited thereto.

The organic film containing the compound represented by formula 1 may have a thickness of 10 μm or less, preferably 0.5 μm or less, and more preferably 0.001-0.5 μm.

The compound represented by formula 1 may be used together with other known materials that function as materials for hole injection, hole transport, light emitting, electron transport or electron injection (if necessary).

The OLED according to the present invention may have a structure having an organic film including a hole injection layer, a hole transport layer, a light emitting layer, an electron transport layer, an electron injection layer and a buffering layer disposed between an anode and the hole injection layer. However, the structure of OLED is not limited thereto and the number of layers included in the organic film may be reduced.

According to the invention, organic light emitting devices (OLED) may have structures as shown in FIGS. 1 to 5, but the embodiments shown in the figures are not limitative.

FIG. 1 shows an OLED having a structure in which an anode 102, a light emitting layer 105 and a cathode 107 are laminated successively on a substrate 101.

Figure 2:
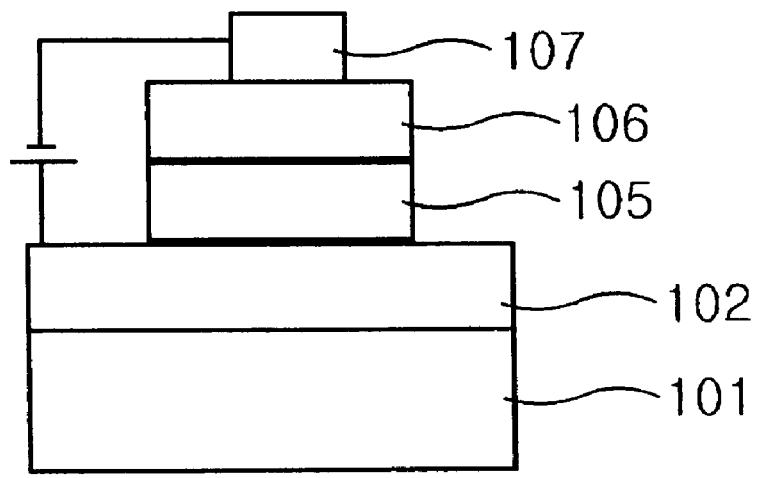

FIG. 2 shows an OLED having a structure in which an anode 102, a hole transport/light emitting layer 105, a light emitting/electron transport layer 106 and a cathode 107 are laminated successively on a substrate 101.

Figure 3:
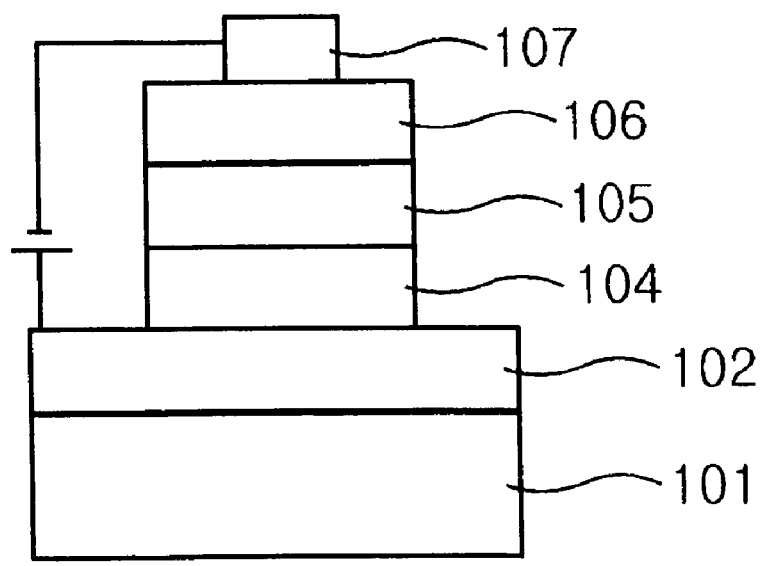

FIG. 3 shows an OLED having a structure in which an anode 102, a hole transport layer 104, a light emitting layer 105, an electron transport layer 106 and a cathode 107 are laminated successively on a substrate 101.

Figure 4:
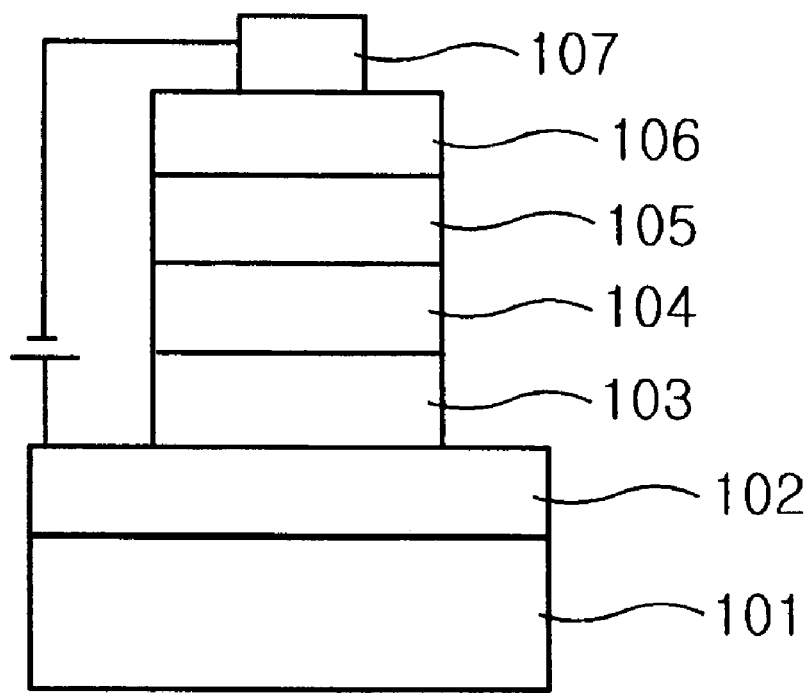

FIG. 4 shows an OLED having a structure in which an anode 102, a hole injection layer 103, a hole transport layer 104, a light emitting layer 105, an electron transport layer 106 and a cathode 107 are laminated successively on a substrate 101.

Figure 5:
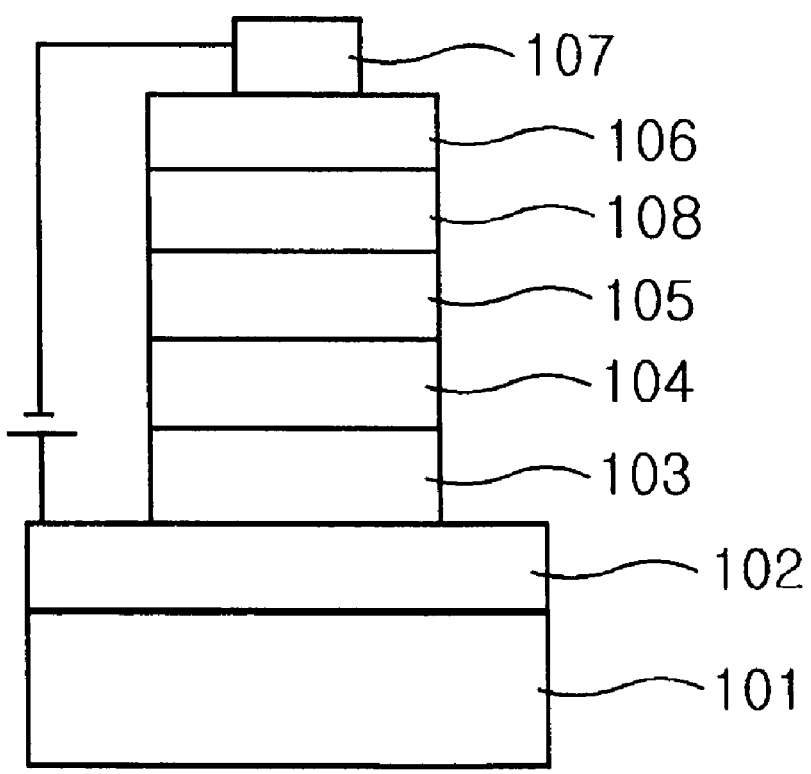
Figure 6:
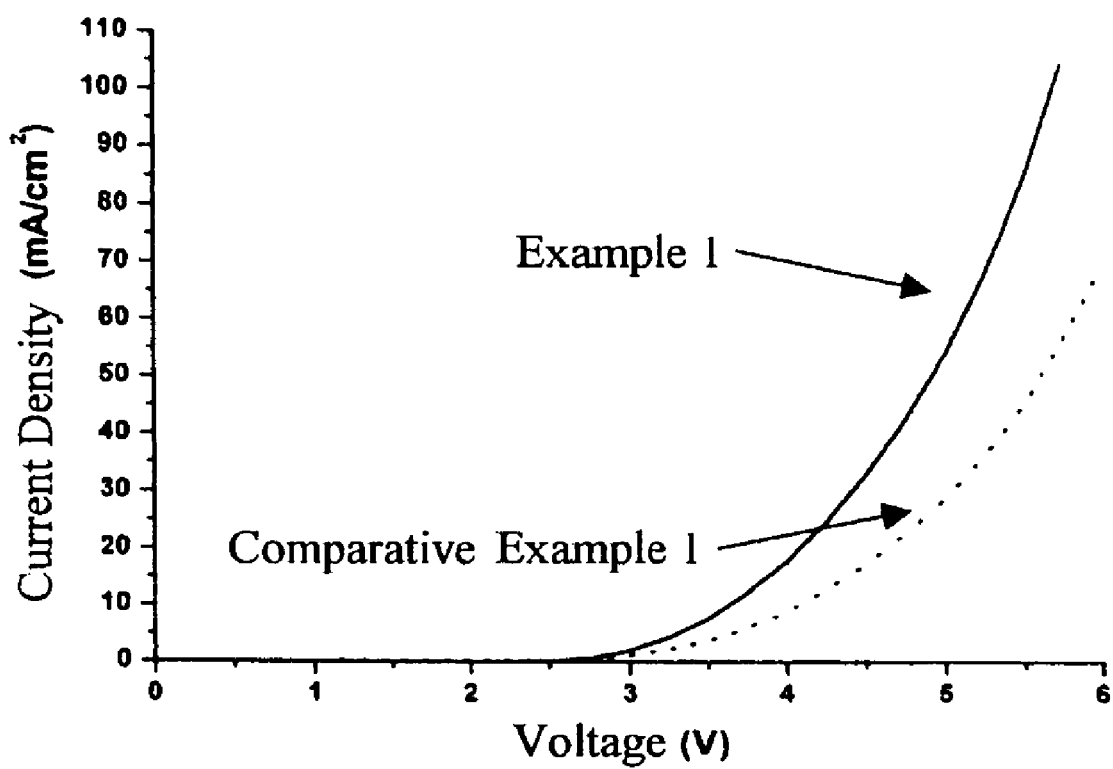
FIG. 6 is a graph showing the current-voltage relationship of the OLED according to Example 1 and that of the OLED according to Comparative Example 1.

FIG. 5 shows an OLED having a structure in which an anode 102, a hole injection layer 103, a hole transport layer 104, a light emitting layer 105, a hole block layer 108, an electron transport layer 106 and a cathode 107 are laminated successively on a substrate 101.

In the structures illustrated in FIGS. 1 to 5, the compound represented by formula 1 may form the hole injection layer 103, hole transport layer 104, light emitting layer 105, hole block layer 108, electron transport layer 106, electron transport/light emitting layer 105 and/or light emitting/electron transport layer 106.

As shown in FIGS. 1 to 5, OLEDs according to the present invention have a structure in which an anode, a multi-layered organic film and a cathode are successively laminated. Additionally, an insulation layer or adhesive layer may be inserted into the interface between each electrode and the organic film. Further, the hole transport layer present in the organic film may be formed of two layers each having a different value of ionization potential.

OLEDs according to the present invention can be prepared by forming an organic film and electrodes by using materials and methods known to one skilled in the art, with the proviso that at least one layer of the organic film contains the compound according to the present invention.

For example, substrates 101 that may be used include a silicon wafer, quartz or glass panel, metal panel, plastic film or sheet, etc.

Materials for anode 102 may include metals such as vanadium, chrome, copper, zinc and gold or alloys thereof; metal oxides such as zinc oxide, indium oxide, indium tin oxide (ITO) and indium zinc oxide; metal/oxide composites such as ZnO:Al or $SnO_2$:Sb; and conductive polymers such as poly (3-methylthiophene), poly[3,4-(ethylene-1,2-dioxy) thiophene] (PEDT), polypyrrole and polyaniline, but are not limited thereto.

Materials for cathode 107 may include metals such as magnesium, calcium, sodium, potassium, titanium, indium, yttrium, lithium, gadolinium, aluminum, silver, tin and lead or alloys thereof; and multi-layered materials such as LiF/Al or $LiO_2$/Al, but are not limited thereto.

Advanced Effect

According to the present invention, it is possible to provide an organic substance capable of carrying out at least one function selected from the group consisting of hole injection, hole transport, hole block, light emitting, electron transport, electron injection, and buffering between an anode and a hole injection layer through molecular designs using a cyclic trimer core structure represented by formula 1. Further, it is possible to improve durability and/or efficiency of an organic light emitting device by using the organic substance in an organic film of the device.

Mode for Carrying Out the Invention

Hereinafter, the present invention will be explained in more detail through Preparation Examples 1-6, Examples 1 and 2, and Comparative Examples 1 and 2. It is to be understood that the following examples are illustrative only and the present invention is not limited thereto.

PREPARATION EXAMPLE 1

Synthesis of Compounds of Formula 1-1
(Trimerization of 2-chlorobenzimidazole)

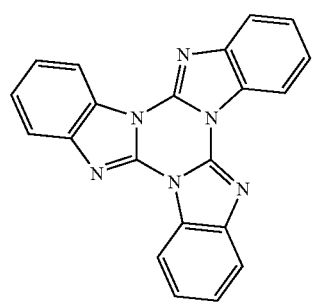

[Formula 1-1]

5 g (0.0327 mole) of 2-chlorobenzimidazole as a starting material was introduced into a 50 mL long-necked flask and the flask was immersed in an oil bath preheated to 195° C. Hereupon, the starting material was dissolved and transformed back into a solid state immediately, while generating hydrogen chloride gas. When the gas stopped bubbling, the reaction mixture was cooled to room temperature and the resultant solid compound was recrystallized with nitrobenzene. Then, the product was filtered, washed with ethanol and ether in turn then dried under vacuum to obtain the compound represented by formula 1-1 as a white solid (2.5 g, yield 50%).

The analysis results for the compound are as follows: m.p. 391-393° C.; $^1$H NMR (500 MHz, DMSO-d6) 8.51 (d, 3H), 7.96 (d, 3H), 7.59 (m, 6H); MS [M+1] 348.

PREPARATION EXAMPLE 2

Synthesis of Compound of Formula
1-5(Trimerization of
1-iodo-2-chloro-4,5-dicyanoimidazole)

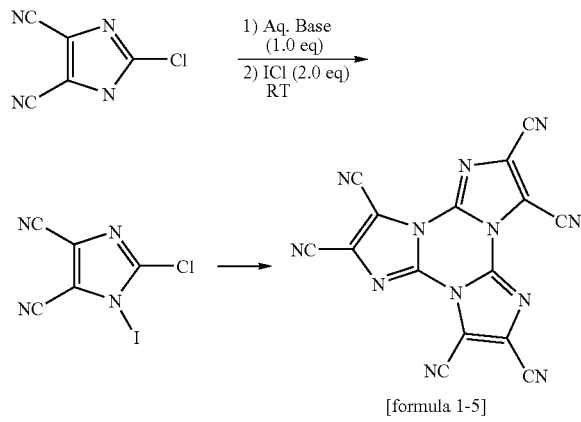

[formula 1-5]

10 g (0.036 mole) of 1-iodo-2-chloro-4,5-dicyanoimidazole as a starting material was introduced into a 50 mL long-necked flask equipped with a sublimation device. Then, the flask was purged with nitrogen continuously two times under vacuum and immersed in an oil bath preheated to 220-240° C. After maintaining the above temperature for 5 hours, $I_2$ and ICl as halogen decomposition products were formed on a cold finger. After cooling back to room temperature, the flask was purged with nitrogen under vacuum. The resultant brown solid was pulverized and 10% $Na_2S_2O_3$ (40 mL) was added thereto. Then, the mixture was stirred for 30 minutes at room temperature and then filtered (three times). The filtered solid was washed with water repeatedly and then dried under vacuum to obtain the compound represented by formula 1-5 as a yellowish brown solid (2.92 g, yield 70%).

The analysis results for the compound were as follows: purity 99.6%; m.p. >400° C.; $^{13}$C NMR (400 MHz, DMSO-d$_6$, ppm) 135.0, 123.2, 110.3, 106.5, 106.2

PREPARATION EXAMPLE 3

Synthesis of Compound of Formula 1-6
(Trimerization of 4,5-diphenylimidazole)

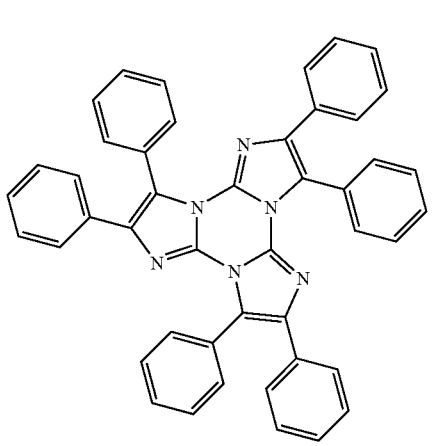

[Formula 1-6]

2.0 g (0.0091 mole) of 4,5-diphenylimidazole as a starting material, 0.01 g of dichloropalladium, 0.3 g of sulfur, 0.1 mL of phenylthioether and 10 mL of phenylether were introduced into a 50 mL round-bottom flask equipped with a condenser. The reaction mixture was reacted under reflux and then cooled. Then, 50 mL of ether was added thereto to form precipitate. The precipitate was removed by using a depressurized filter and then the filtrate was distilled under reduced pressure to remove all solvents therefrom. Then, the resultant product was dissolved into 10 mL of dioxane at 90-100° C. and 15 mL of acetic acid was added thereto to perform recrystallization. The resultant product was filtered by using a depressurized filter to obtain a dark gray solid. The dark gray solid was purified by sublimation to obtain the compound represented by formula 1-6 as a greenish white solid (0.6 g, yield 30%).

The analysis results for the compound were as follows: purity 99.6%; m.p. 361-363° C.; $^1$H NMR (400 MHz, DMSO-d$_6$) 7.60-7.64 (m, 5H), 7.23-7.16 (m, 5H); MS [M+1]$^+$ 655, [M]$^-$ 654

PREPARATION EXAMPLE 4

Synthesis of compound of formula 1-12

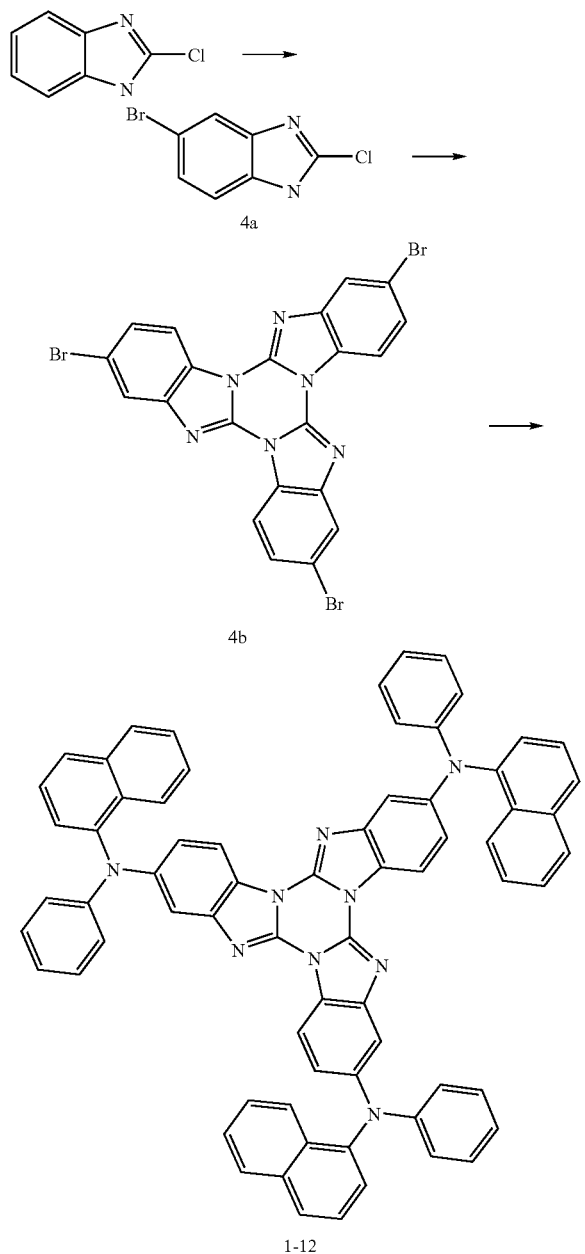

1-12

(1) Synthesis of Compound of Formula 4a

To a mixture containing 2-chlorobenzimidazole (0.763 g, mmol) as a starting material dissolved in 25 mL of methanol, bromine/methanol solution (0.26 mL/5 mL) was gradually added dropwise. Then, the reaction mixture was stirred for 5 hours at room temperature. After checking a reaction degree by HPLC, 25 mL of water was added and the mixture was stirred for 18 hours at room temperature. The resultant precipitate was filtered and washed with cold water repeatedly until it became neutral. Then, the resultant product was recrystallized with methanol/water (1:1) solution to obtain the compound of formula 4a as a white solid (0.6 g, yield 52.0%).

The analysis results for the compound were as follows: m.p. 228-230° C.; $^1$H NMR (400 MHz, DMSO-$d_6$) 7.73 (s, 1H), 7.49-7.47 (d, 1H), 7.39-7.36 (d, 1H); MS [M+1]$^+$ 231

(2) Synthesis of Compound of Formula 4b (Trimerization of 5-bromo-2-chlorobenzimidazole)

1.1 g (4.7 mmole) of 5-bromo-2-chlorobenzimidazole as a starting material was introduced into a 50 mL long-necked flask and was immersed in an oil bath preheated to 230° C. Hereupon, the starting material was dissolved and transformed back into a solid state immediately, while generating hydrogen chloride gas. When the gas stopped bubbling, the reaction mixture was cooled to room temperature and the resultant solid compound was recrystallized with nitrobenzene. Then, the product was filtered, washed with ethanol and ether in turn and then dried under vacuum to obtain the compound represented by formula 4b as a pale yellow solid (0.43 g, yield 47%).

The analysis results for the compound are as follows: m.p. 354° C.; MS [M+1] 583 (isomer)

(3) Synthesis of Compound of Formula 1-12

To a 50 mL round-bottom flask equipped with a condenser, sequentially added were a mixed solution containing 10 mL of mesitylene and the compound of formula 4b (0.4 g, 0.68 mmol), 50 mg of Pd$_2$(dba)$_3$ (0.005 mmol), 17 mg of P(t-Bu)$_3$ (0.081 mmol), and 0.28 g of Na(t-OBu) (3 mmol). The reaction mixture was reacted for 5 hours at 120° C. After the reaction mixture was cooled to room temperature, 20 mL of toluene and 30 mL of water were added thereto to perform phase separation. The organic layer obtained from the preceding step was dried over MgSO$_4$ and the dried product was distilled under reduced pressure to remove all solvents therefrom. The product was separated by column chromatography and then washed with ethanol to obtain the compound of formula 1-12 as a white solid (200 mg, yield 30%).

The analysis results for the compound were as follows: m.p. ≧350° C.; $^1$H NMR (500 MHz, DMSO-d6) 8.27-8.15 (m, 1H), 8.09-7.74 (m, 3H), 7.63-7.16 (m, 8H), 6.97-6.86 (m, 3H); MS [M+1] 1000

PREPARATION EXAMPLE 5

Synthesis of compound of formula 1-46

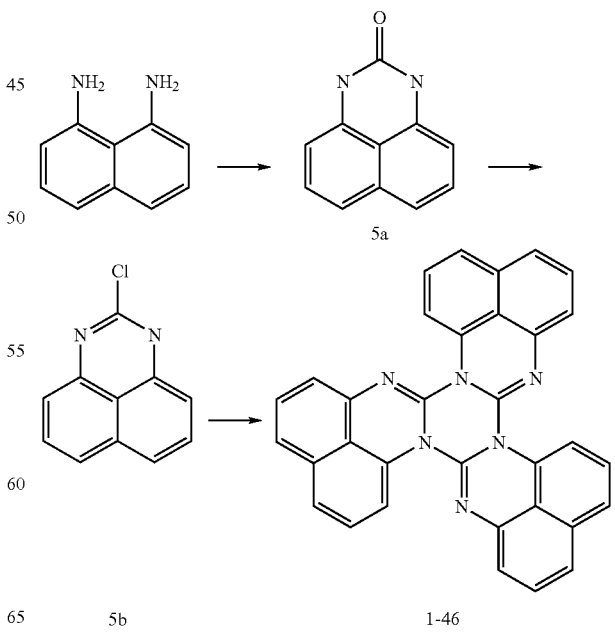

(1) Synthesis of Compound of Formula 5b (2-chloroperimidine)

Purified 1,8-diaminonaphthalene (1.7 g, 10.7 mmol) was introduced into 30 mL of diluted hydrochloric acid solution (0.5N) and heated to be completely dissolved. After 10 mL of aqueous sodium cyanide solution (0.7 g, 10.7 mmol) was gradually added thereto, red precipitate was formed. The red precipitate was heated for 1 hour and cooled. Then, the resultant precipitate was filtered, washed with ether and then dried under vacuum to obtain 2-perimidinone (5a) as a pale reddish white solid (1.12 g, 6.1 mmol, yield 57%). The resultant solid was added to 10 mL of phosphorous oxychloride ($POCl_3$) and refluxed for 3 hours by heating. Then, excessive amount of phosphorous oxychloride was removed by vacuum distillation. The residue was dispersed in water and neutralized with 2N aqueous ammonia to form yellow precipitate. The precipitate was filtered and the filtrate was precipitated again by using THF and hexane as solvents. Then, the solution was filtered again and the filtered product was dried under vacuum to obtain 2-chloroperimidine as a light yellow solid (0.6 g, 2.9 mmol, yield 50%).

The analysis results for the above compounds were as follows:

2-perimidinone (5a): $^1$H NMR (400 MHz, DMSO-$d_6$), 10.06 (s, 2H), 7.21 (t, J=7.6 Hz, 2H), 7.10 (d, J=8.4 Hz, 2H), 6.51 (d, J=7.6 Hz, 2H)

2-chloroperimidine (5b): $^1$H NMR (400 MHz, DMSO-$d_6$), 11.35 (s, 1H), 7.20-7.08 (m, 4H), 6.60 (d, J=6.4 Hz, 1H), 6.38 (d, J=6.8 Hz, 1H)

(2) Synthesis of Compound of Formula 1-46

2-chloroperimidine (0.73 g, 3.6 mmol) was introduced into a flask equipped with a mechanical stirrer under nitrogen atmosphere and heated to 210° C. to dissolve it. After stirring for 10 minutes, the mixture turned dark red. About 20 mL of nitrobenzene was added thereto, and the mixture was stirred for about 1 hour, cooled and filtered to separate precipitate. The filtered product was washed sufficiently with nitrobenzene, saturated sodium carbonate solution, water, ethanol and THF, in turn, and then was dried under vacuum to obtain 0.57 g of the compound represented by formula 1-46 as a red solid (yield 32%).

The analysis results for the compound were as follows: $^1$H NMR (400 MHz, DMSO-$d_6$), 7.52-7.28 (m, 12H), 6.94-6.80 (m, 6H); MS (M+HCl+H) 535

EXAMPLE 1

(Manufacture of Organic Light Emitting Device)

A glass substrate on which a thin film of ITO (indium tin oxide) was coated to a thickness of 1500 Å was immersed in distilled water containing a detergent to wash the substrate with ultrasonic waves for 30 minutes. Next, washing with ultrasonic waves was repeated for 10 minutes and two times by using distilled water. The detergent was a product commercially available from Fisher Co. The distilled water has been filtered previously by using a filter commercially available from Millipore Co. After the completion of washing with distilled water, washing with ultrasonic waves was carried out by using solvents such as isopropyl alcohol, acetone and methanol, in turn. The resultant product was dried and transferred to a plasma cleaner. Then, the substrate was cleaned for 5 minutes by using nitrogen plasma and transferred to a vacuum deposition device.

On the ITO transparent electrode prepared as described above, hexanitrile hexaazatriphenylene represented by the following formula 4 was coated to a thickness of 500 Å by thermal vacuum deposition, thereby forming a hole injection layer. Next, NPB as a hole transport material was coated thereon to a thickness of 400 Å by vacuum deposition. Additionally, a light emitting compound (Alq3) represented by the following formula 5 was coated thereon to a thickness of 300 Å by vacuum deposition to form a light emitting layer. On the light emitting layer, the compound represented by formula 1-1 was coated to a thickness of 200 Å by vacuum deposition to form an electron injection/transport layer. Next, on the electron injection/transport layer, lithium fluoride (LiF) and aluminum were sequentially vacuum-deposited to a thickness of 10 Å and 2500 Å, respectively, to form a cathode. In the above process, deposition rate of each organic substance was maintained at 1 Å/sec and deposition rates of lithium fluoride and aluminum were maintained at 0.2 Å/sec and 3-7 Å/sec, respectively.

[Formula 4]

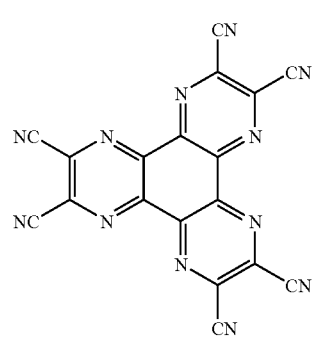

[Formula 5]

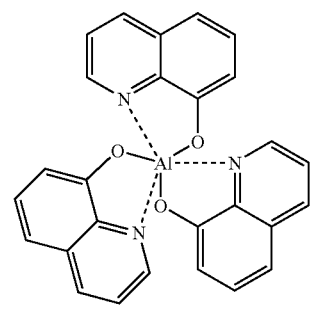

The resultant organic light emitting device showed a drive voltage of 3.57V at a forward current density of 10 mA/cm$^2$. Further, specific green spectrum of Alq3 was observed with x=3.94 and y=0.56 based on the 1931 CIE color coordinate. Such light emitting operation of the device at the above drive voltage indicates that the compound of formula 1-1 contained in the layer disposed between the light emitting layer and the cathode can function as an electron injection/transport material.

Comparative Example 1

Example 1 was repeated to manufacture an organic light emitting device, except that Alq3, a conventional compound useful for electron injection and transport was coated on the light emitting layer to a thickness of 200 Å by vacuum deposition, instead of the compound of formula 1-1, to form an electron injection/transport layer.

The resultant organic light emitting device showed a drive voltage of 4.12V at a forward current density of 10 mA/cm$^2$. Further, specific green spectrum of Alq3 was observed with x=0.34 and y=0.56 based on the 1931 CIE color coordinate.

The following Table 1 shows the results of variations in drive voltage depending on currents for the organic light emitting devices obtained from Example 1 and Comparative Example 1.

TABLE 1

| Current density (mA/cm$^2$) | Example 1 Voltage (V) | Comp. Ex. 1 Voltage (V) |
|---|---|---|
| 10 | 3.57 | 4.12 |
| 50 | 4.82 | 5.67 |
| 100 | 5.62 | 6.59 |

As can be seen from Table 1, when an electron injection/transport layer for an organic light emitting device is formed by using the compound of formula 1-1, the drive voltage can be reduced under the same current density, compared to an organic light emitting device using Alq3 that is a conventional material functioning as an electron injection/transport layer.

EXAMPLE 2

On the ITO transparent electrode prepared as described in Example 1, hexanitrile hexaazatriphenylene represented by formula 4 was coated to a thickness of 500 Å by thermal vacuum deposition, thereby forming a hole injection layer. Next, the compound of formula 1-12 obtained from Preparation Example 4, as a hole transport material, was coated thereon to a thickness of 200 Å by vacuum deposition. Additionally, a light emitting compound (Alq3) represented by formula 5 was coated thereon to a thickness of 300 Å by vacuum deposition to form a light emitting layer. On the light emitting layer, the compound represented by the following formula 6 was coated to a thickness of 200 Å by vacuum deposition to form an electron injection/transport layer. Next, on the electron injection/transport layer, lithium fluoride (LiF) and aluminum were sequentially vacuum-deposited to a thickness of 10 Å and 2500 Å, respectively, to form a cathode. In the above process, deposition rate of each organic substance was maintained at 1 Å/sec and deposition rates of lithium fluoride and aluminum were maintained at 0.2 Å/sec and 3-7 Å/sec, respectively.

[Formula 6]

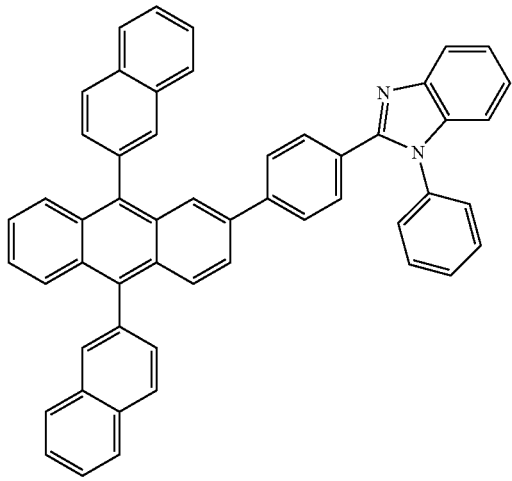

The resultant organic light emitting device showed a light emitting efficiency of 460 cd/cm$^2$ at a forward current density of 100 mA/cm$^2$. Further, specific green spectrum of Alq3 was observed with x=0.32 and y=0.56 based on the 1931 CIE color coordinate. Such light emitting operation of the device at the above drive voltage indicates that the compound of formula 1-12 contained in the layer disposed between the hole injection layer and the light emitting layer can function as a hole transport material.

Comparative Example 2

Example 2 was repeated to manufacture an organic light emitting device, except that NPB, a conventional compound useful for hole transport was coated on the hole injection layer to a thickness of 200 Å by vacuum deposition, instead of the compound of formula 1-12, to form a hole transport layer.

The resultant organic light emitting device showed a light emitting efficiency of 340 cd/cm$^2$ at a forward current density of 100 mA/cm$^2$. Further, specific green spectrum of Alq3 was observed with x=0.32 and y=0.56 based on the 1931 CIE color coordinate.

As can be seen from Example 2 and Comparative Example 2, when an organic light emitting device includes the compound represented by formula 1-12 in a hole transport layer, the light emitting efficiency can be improved under the same current density, compared to an organic light emitting device including NPB in a hole transport layer.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. An organic light emitting device including a first electrode, an organic film having one or more layers and a second electrode, laminated successively, wherein at least one layer of the organic film includes at least one compound represented by Formula 1:

[Formula 1]

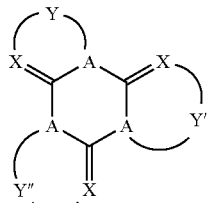

wherein A is B or N; X is N or CR$_0$, wherein R$_0$ is selected from the group consisting of a hydrogen atom (H), halogen atom, nitrile group (CN), nitro group (NO$_2$), formyl group, acetyl group, benzoyl group, amide group, styryl group, acetylene group, quinoline group, quinazoline group, phenanthroline group, cuproine group, anthraquinone group, benzoquinone group, quinone group, acridine group, substituted or non-substituted alkyl group, substituted or non-substituted aryl group, substituted or non-substituted aralkyl group, substituted or non-substituted arylamine group, substituted or non-substituted alkylamine group, substituted or non-substituted aralkylamine group, and substituted or non-substituted heterocyclic group; and wherein each of Y, Y' and Y" represents a substituted or non-substituted aromatic heterocycle that includes a 5-membered aromatic heterocycle containing A and X as ring members or a 6-membered aromatic heterocycle containing A and X as ring members, wherein Y, Y' and Y" are identical or different.

2. The organic light emitting device according to claim 1, wherein each of Y, Y' and Y" is substituted with one or more identical or different substituents selected from the group consisting of a halogen atom, nitrile group (CN), nitro group (NO$_2$), formyl group, acetyl group, benzoyl group, amide group, styryl group, acetylene group, quinoline group, quinazoline group, phenanthroline group, cuproine group, anthraquinone group, benzoquinone group, quinone group, acridine group, substituted or non-substituted alkyl group, substituted or non-substituted aryl group, substituted or non-substituted aralkyl group, substituted or non-substituted arylamine group, substituted or non-substituted alkylamine group, substituted or non-substituted aralkylamine group, and substituted or non-substituted heterocyclic group, wherein two substituents adjacent to each other are not fused or form a fused ring together.

3. The organic light emitting device according to claim 1, wherein the compound is represented by formula 2:

[Formula 2]

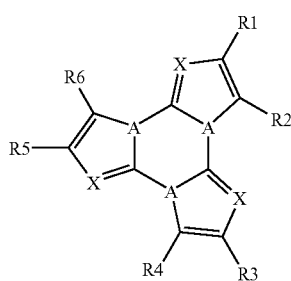

wherein

A and X are the same as defined in claim 1; and

R1 to R6 are identical or different and each is selected from the group consisting of a hydrogen atom (H), halogen atom, nitrile group (CN), nitro group (NO$_2$), formyl group, acetyl group, benzoyl group, amide group, styryl group, acetylene group, quinoline group, quinazoline group, phenanthroline group, cuproine group, anthraquinone group, benzoquinone group, quinone group, acridine group, substituted or non-substituted alkyl group, substituted or non-substituted aryl group, substituted or non-substituted aralkyl group, substituted or non-substituted arylamine group, substituted or non-substituted alkylamine group, substituted or non-substituted aralkylamine group, and substituted or non-substituted heterocyclic group, wherein R1 and R2, R3 and R4, and R5 and R6 optionally form a fused ring with each other.

4. The organic light emitting device according to claim 1, wherein the compound is represented by formula 3:

[Formula 3]

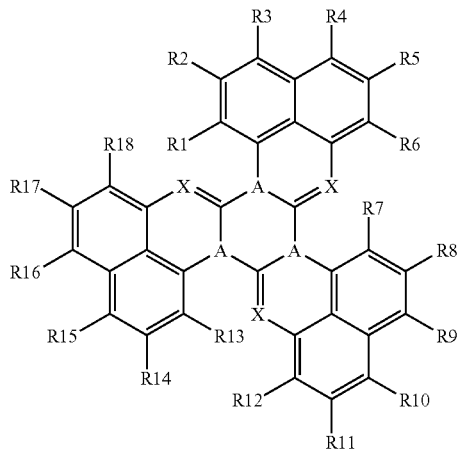

wherein

A and X are the same as defined in claim 1; and

R1 to R18 are identical or different and each is selected from the group consisting of a hydrogen atom (H), halogen atom, nitrile group (CN), nitro group (NO$_2$), formyl group, acetyl group, benzoyl group, amide group, styryl group, acetylene group, quinoline group, quinazoline group, phenanthroline group, cuproine group, anthraquinone group, benzoquinone group, quinone group, acridine group, substituted or non-substituted alkyl group, substituted or non-substituted aryl group, substituted or non-substituted aralkyl group, substituted or non-substituted arylamine group, substituted or non-substituted alkylamine group, substituted or non-substituted aralkylamine group, and substituted or non-substituted heterocyclic group, wherein each of R1 to R18 optionally form a fused ring together with a substituent adjacent thereto.

5. The organic light emitting device according to claim 1, wherein the compound is selected from the group consisting of compounds represented by formulae 1-1 to 1-18 and 1-20 to 1-46:

[Formula 1-1]

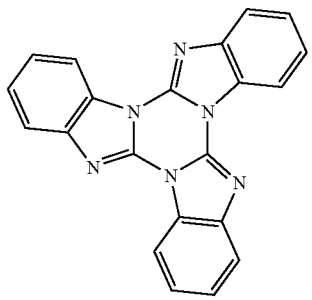

[Formula 1-2]

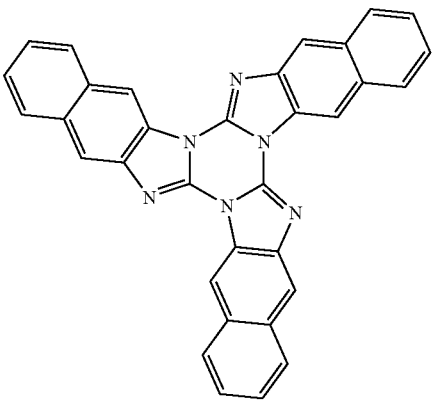

[Formula 1-3]
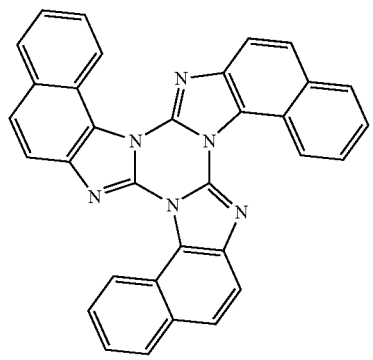
[Formula 1-4]
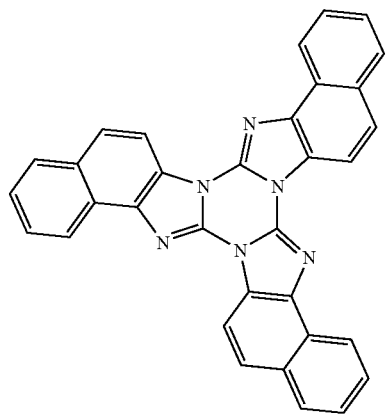
[Formula 1-5]
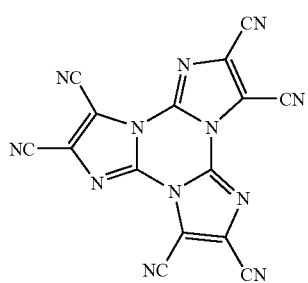
[Formula 1-6]
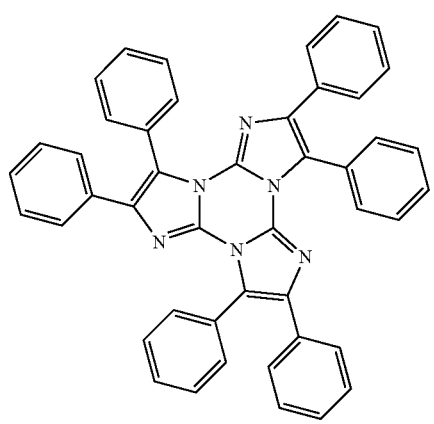
[Formula 1-7]
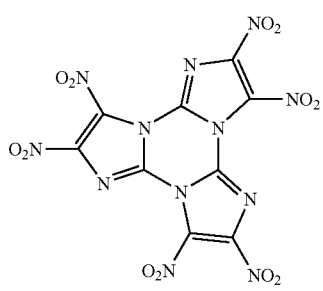
[Formula 1-8]
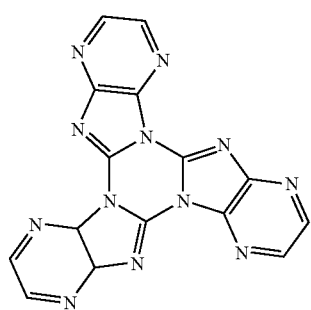

-continued
[Formula 1-9]
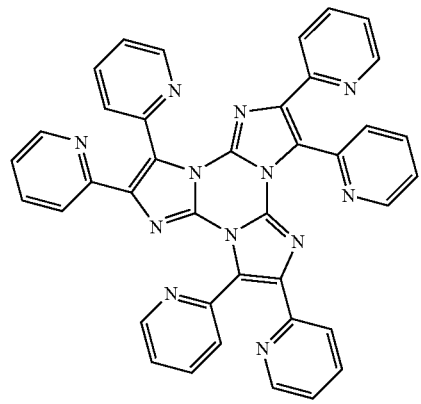
[Formula 1-10]
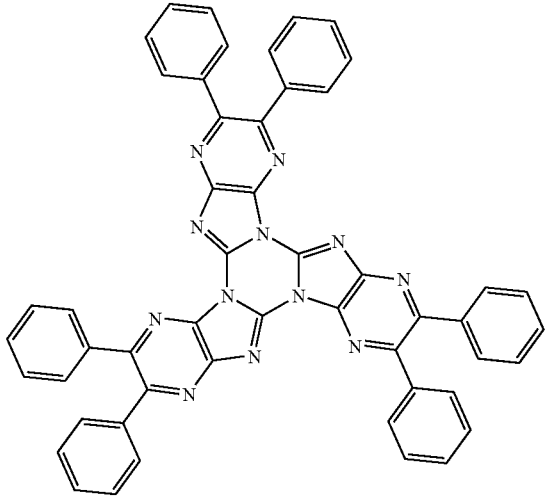
[Formula 1-11]
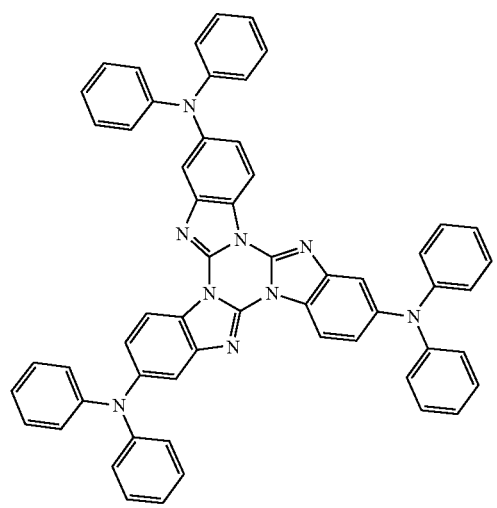
[Formula 1-12]
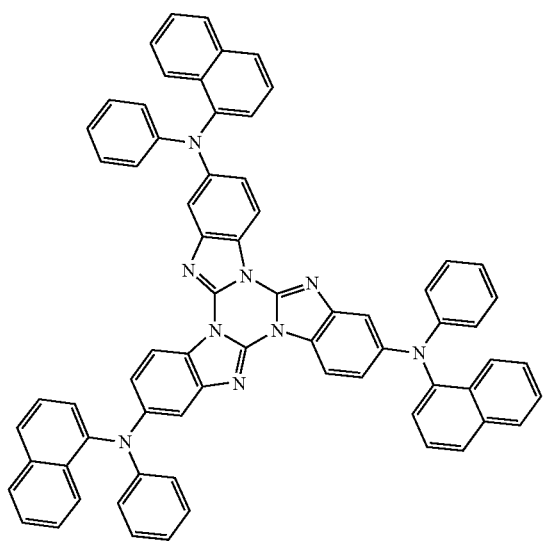
[Formula 1-13]
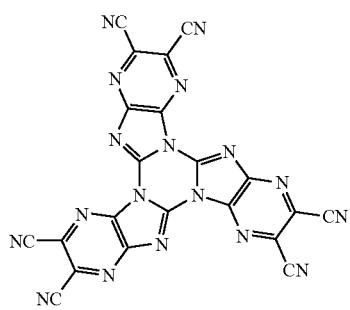
[Formula 1-14]
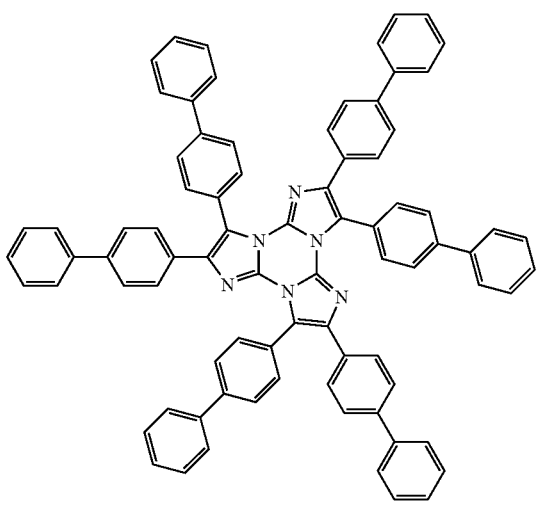

[Formula 1-15]
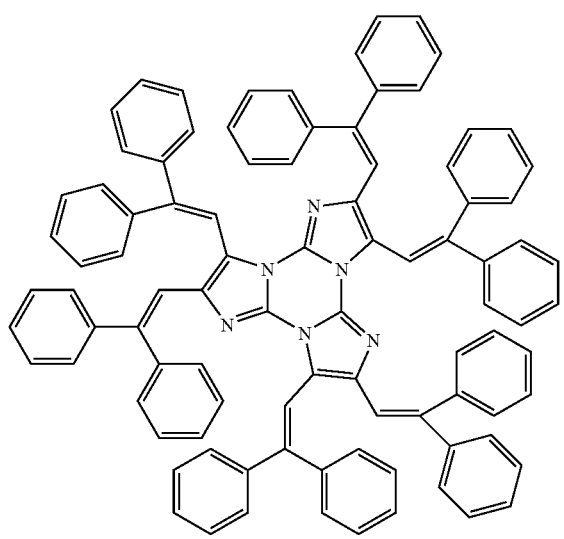
[Formula 1-16]
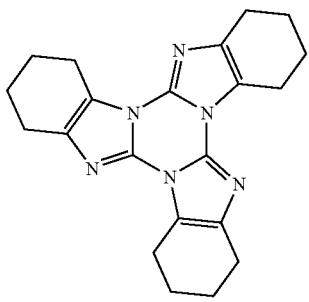
[Formula 1-17]
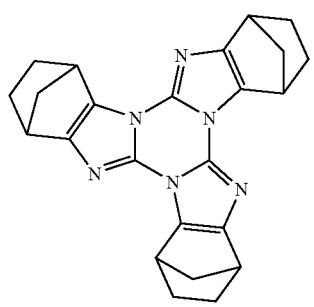
[Formula 1-18]
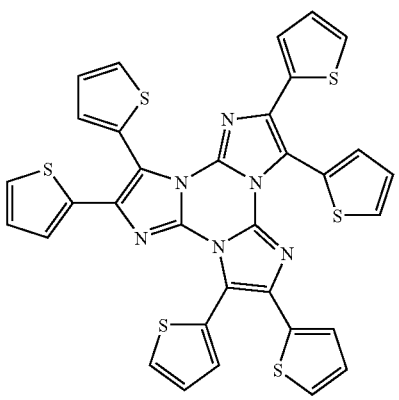
[Formula 1-20]
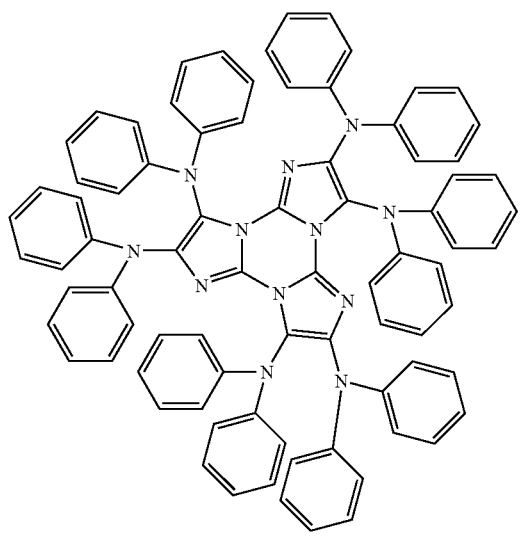

-continued
[Formula 1-21]
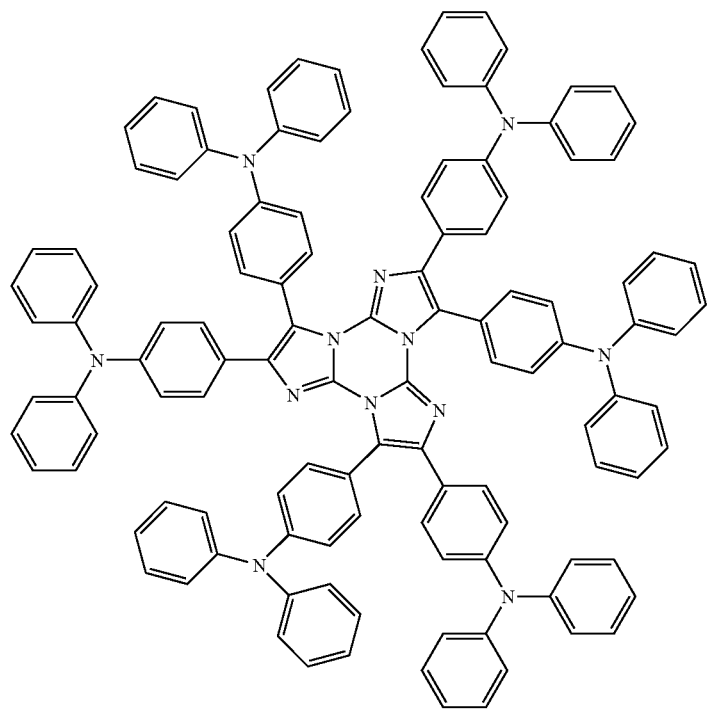
[Formula 1-22]
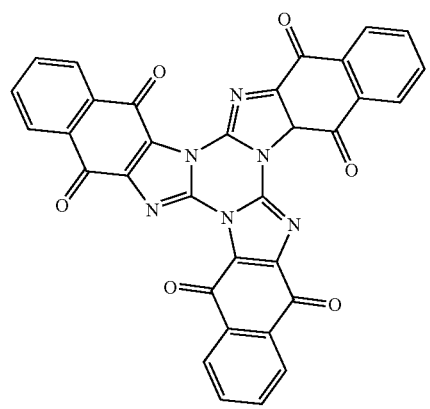
[Formula 1-23]
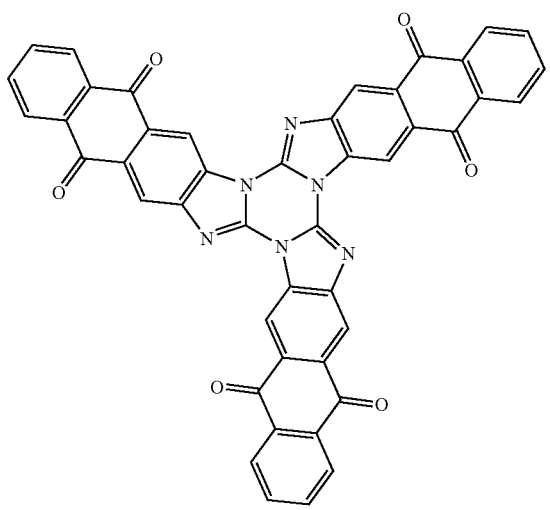
[Formula 1-24]
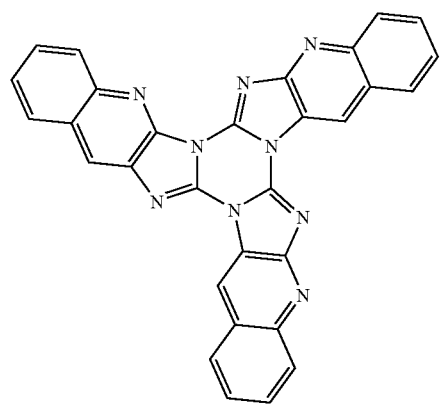
[Formula 1-25]
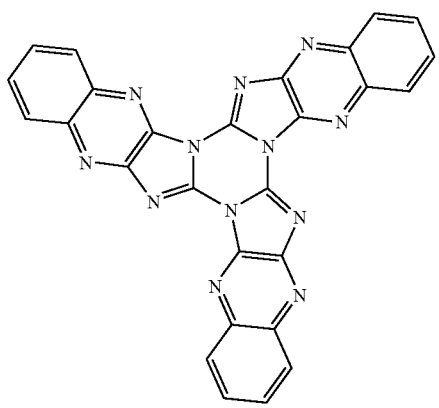

-continued
[Formula 1-26]
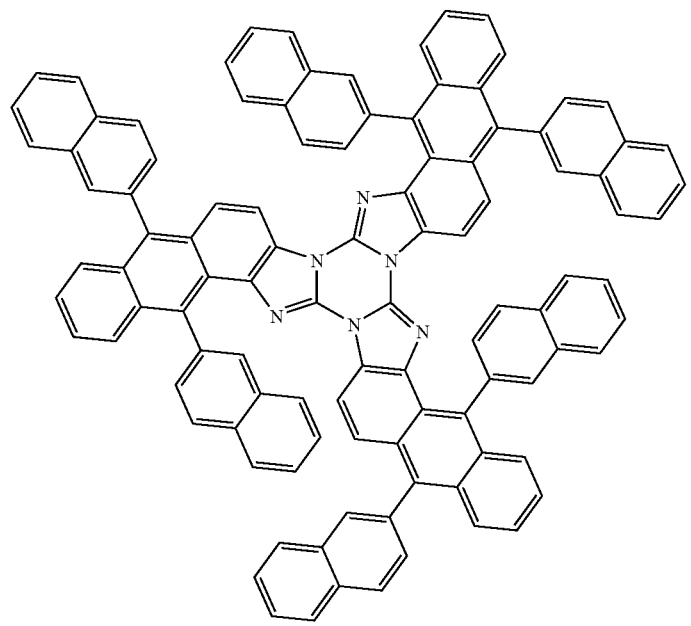
[Formula 1-27]
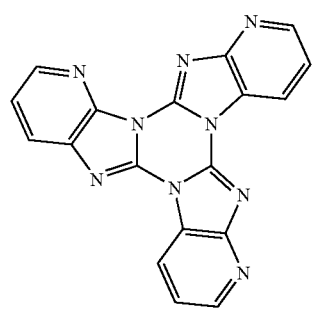
[Formula 1-28]
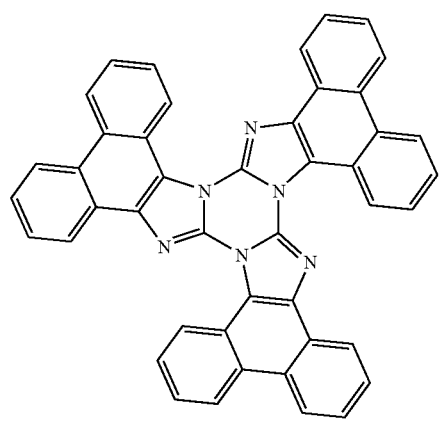

[Formula 1-29]
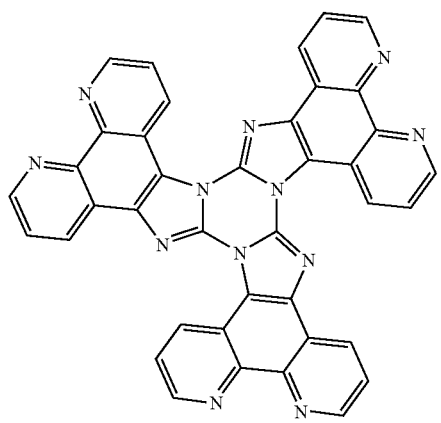
[Formula 1-30]
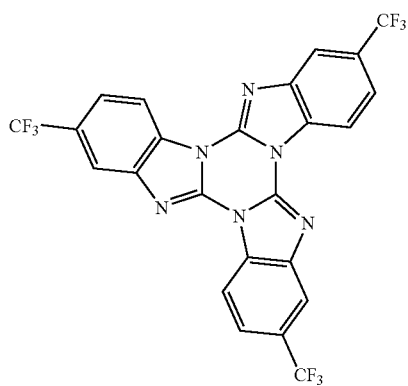
[Formula 1-31]
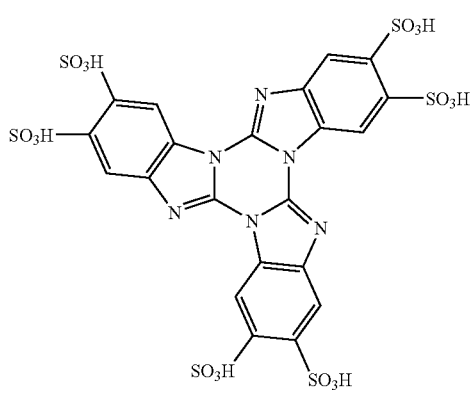
[Formula 1-32]
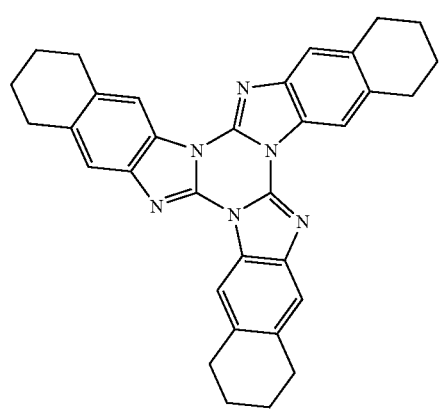
[Formula 1-33]
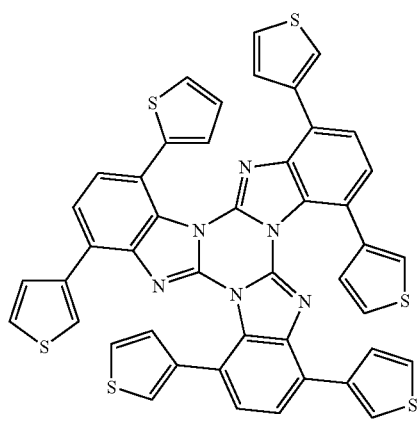

[Formula 1-34]
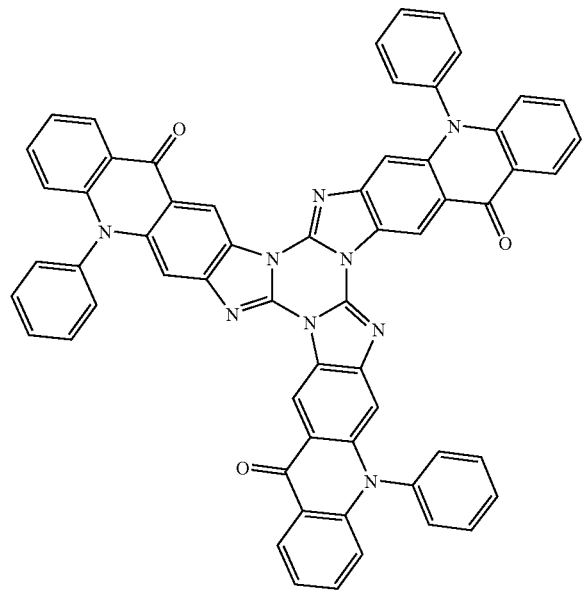
[Formula 1-35]
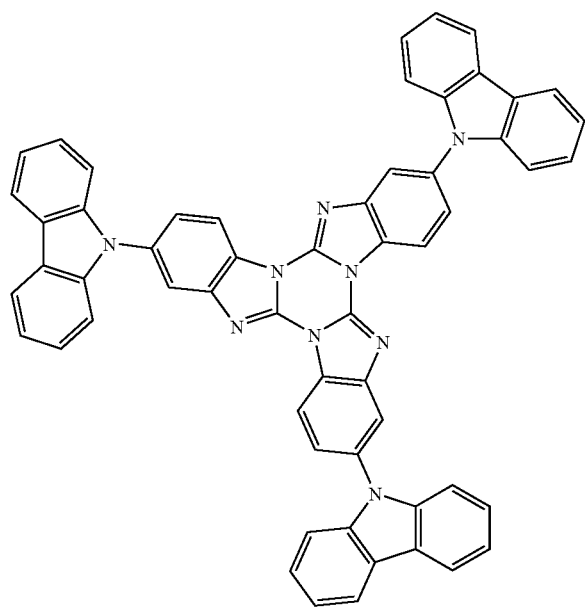
[Formula 1-36]
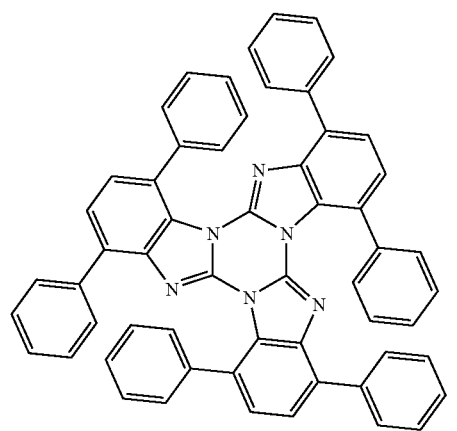
[Formula 1-37]
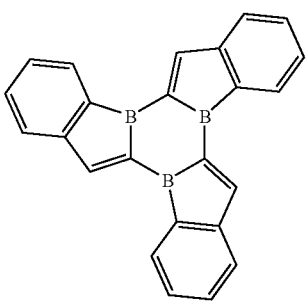

-continued
[Formula 1-38]
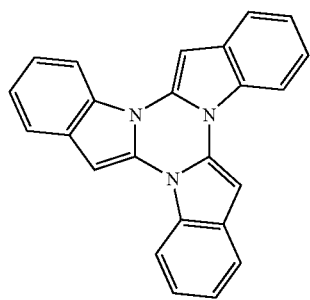
[Formula 1-39]
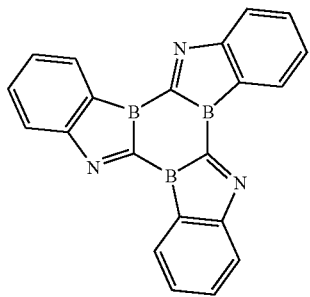
[Formula 1-40]
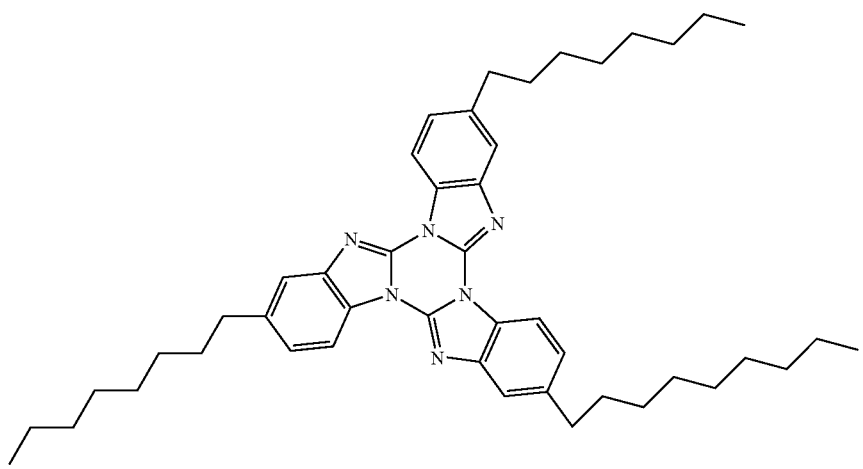
[Formula 1-41]
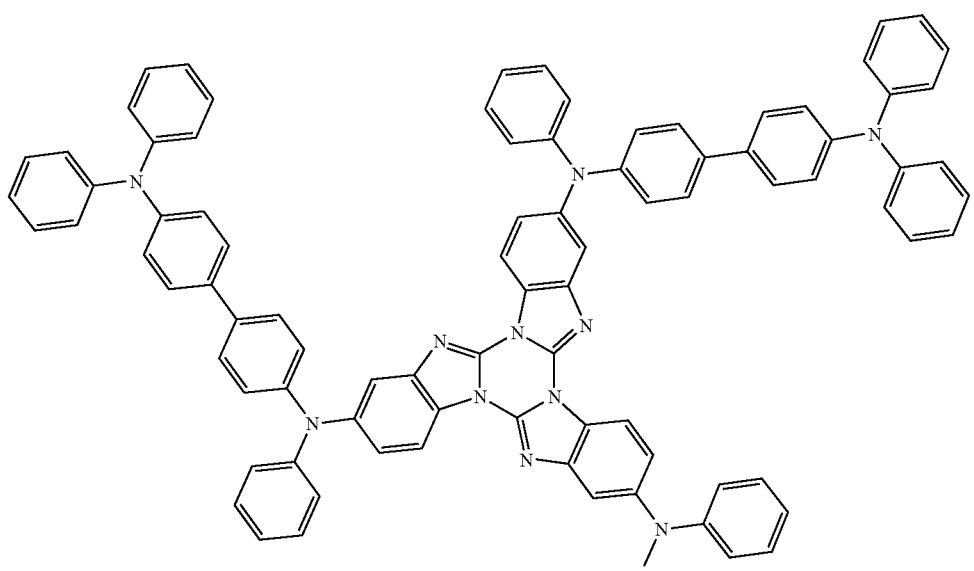

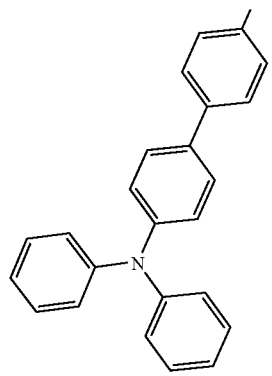
[Formula 1-42]
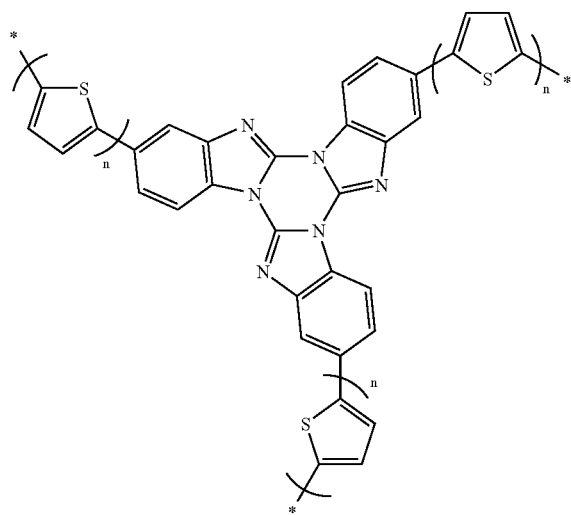
wherein n is an integer of between 1 and 6;
[Formula 1-43]
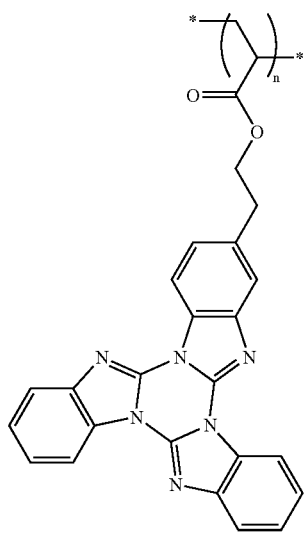
wherein n is an integer of at least 1;
[Formula 1-44]
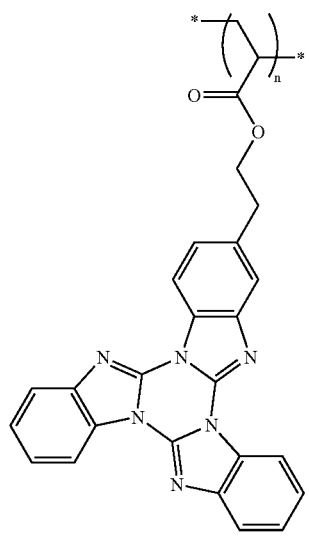
wherein n is an integer of at least 1;

[Formula 1-45]
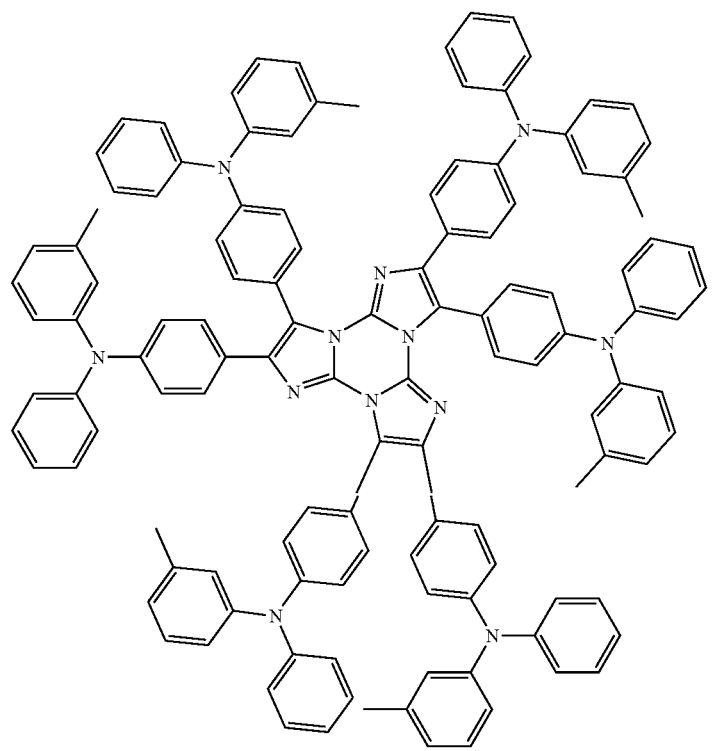
[Formula 1-46]
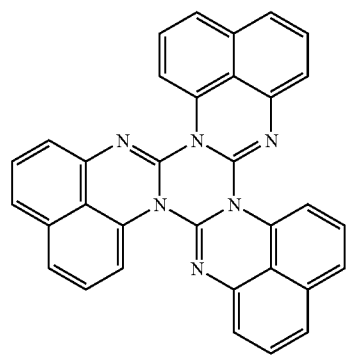
* * * * *